US011808537B2

(12) United States Patent
Teetzel et al.

(10) Patent No.: US 11,808,537 B2
(45) Date of Patent: Nov. 7, 2023

(54) WEAPON SYSTEM WITH OPERATOR IDENTIFICATION

(71) Applicant: Wilcox Industries Corp., Newington, NH (US)

(72) Inventors: James W. Teetzel, Portsmouth, NH (US); Gary M. Lemire, Lee, NH (US); Roula Assadi, Stratham, NH (US)

(73) Assignee: Wilcox Industries Corp., Newington, NH (US)

( * ) Notice: Subject to any disclaimer, the term of this patent is extended or adjusted under 35 U.S.C. 154(b) by 0 days.

(21) Appl. No.: 16/433,224

(22) Filed: Jun. 6, 2019

(65) Prior Publication Data

US 2019/0376755 A1 Dec. 12, 2019

Related U.S. Application Data

(60) Provisional application No. 62/681,486, filed on Jun. 6, 2018.

(51) Int. Cl.

| F41A 17/06 | (2006.01) |
| F41A 17/30 | (2006.01) |
| G06K 7/14 | (2006.01) |
| A61F 11/14 | (2006.01) |
| G06V 40/16 | (2022.01) |

(52) U.S. Cl.
CPC ............ *F41A 17/066* (2013.01); *A61F 11/14* (2013.01); *F41A 17/30* (2013.01); *G06K 7/1417* (2013.01); *G06V 40/172* (2022.01); *A61F 11/145* (2022.01)

(58) Field of Classification Search
CPC .......... F41A 17/066; F41A 17/06; F41G 1/36; F41G 1/00
See application file for complete search history.

(56) References Cited

U.S. PATENT DOCUMENTS

| 3,854,231 A | 12/1974 | Broyles |
| 4,689,911 A | 9/1987 | White |
| 5,062,232 A * | 11/1991 | Eppler .................. F41A 17/063 42/70.11 |
| 5,555,662 A | 9/1996 | Teetzel |
| 6,725,594 B2 | 4/2004 | Hines |
| 7,021,187 B1 | 4/2006 | Grassi |
| 7,627,975 B1 | 12/2009 | Hines |
| 7,975,419 B2 | 7/2011 | Darian |

(Continued)

FOREIGN PATENT DOCUMENTS

| JP | H06111852 A | 4/1994 |
| WO | 2005047801 A2 | 5/2005 |

(Continued)

OTHER PUBLICATIONS

International Search Report and Written Opinion received in PCT/US2017/013402 dated May 15, 2017.

(Continued)

*Primary Examiner* — J. Woodrow Eldred
(74) *Attorney, Agent, or Firm* — McLane Middleton, Professional Association

(57) ABSTRACT

A weapon system for a firearm includes a processor, the processor having an associated memory, and an optical reader, the optical reader configured to receive operator-identification information and transmit the operator-identification information to the processor.

63 Claims, 29 Drawing Sheets

(56) References Cited

U.S. PATENT DOCUMENTS

| | | | |
|---|---|---|---|
| 8,091,265 B1 | 1/2012 | Teetzel et al. | |
| 8,397,418 B2 | 3/2013 | Cabahug et al. | |
| 8,490,313 B2 | 7/2013 | Frascati | |
| 9,062,933 B1 | 6/2015 | Allen et al. | |
| 9,200,867 B1 | 12/2015 | Swan | |
| 9,279,639 B2 | 3/2016 | Hines | |
| 9,651,325 B1* | 5/2017 | Gant | F41A 17/06 |
| 9,841,249 B1 | 12/2017 | Nicks et al. | |
| 9,870,716 B1 | 1/2018 | Rao et al. | |
| 10,175,018 B1* | 1/2019 | Campagna | G06K 9/00268 |
| 2002/0131585 A1 | 9/2002 | Jones et al. | |
| 2006/0191183 A1 | 8/2006 | Griffin | |
| 2007/0017139 A1 | 1/2007 | Larue | |
| 2007/0033851 A1 | 2/2007 | Hochstrate et al. | |
| 2008/0134562 A1 | 6/2008 | Teetzel | |
| 2009/0044439 A1 | 2/2009 | Phillips et al. | |
| 2009/0178325 A1 | 7/2009 | Veilleux | |
| 2009/0188976 A1 | 7/2009 | Gunnarsson et al. | |
| 2010/0192444 A1 | 8/2010 | Cabahug et al. | |
| 2010/0192448 A1 | 8/2010 | Darian | |
| 2011/0010979 A1 | 1/2011 | Houde-Walter | |
| 2011/0136350 A1 | 6/2011 | Palli et al. | |
| 2011/0162245 A1 | 7/2011 | Kamal et al. | |
| 2011/0173865 A1 | 7/2011 | Compton | |
| 2011/0283585 A1 | 11/2011 | Cabahug et al. | |
| 2012/0144716 A1 | 6/2012 | Cabahug et al. | |
| 2012/0180363 A1 | 7/2012 | Frascati et al. | |
| 2012/0194419 A1 | 8/2012 | Osterhout et al. | |
| 2012/0311906 A1 | 12/2012 | Troy et al. | |
| 2013/0036646 A1 | 2/2013 | Rubac | |
| 2013/0061504 A1 | 3/2013 | Malherbe et al. | |
| 2013/0104438 A1 | 5/2013 | Hines | |
| 2013/0104439 A1 | 5/2013 | Hines | |
| 2014/0059911 A1 | 3/2014 | Oh et al. | |
| 2014/0150317 A1 | 6/2014 | Esserman et al. | |
| 2014/0190061 A1 | 7/2014 | Griffin | |
| 2014/0215881 A1 | 8/2014 | Milde et al. | |
| 2014/0360077 A1 | 12/2014 | Miller et al. | |
| 2015/0369554 A1 | 12/2015 | Kramer | |
| 2016/0010949 A1 | 1/2016 | Teetzel et al. | |
| 2016/0054080 A1 | 2/2016 | Haimi | |
| 2016/0061560 A1 | 3/2016 | Saadon | |
| 2016/0084161 A1 | 3/2016 | Lyren | |
| 2016/0153744 A1 | 6/2016 | Teetzel et al. | |
| 2016/0195351 A1 | 7/2016 | Burden | |
| 2016/0209169 A1 | 7/2016 | Toole | |
| 2016/0327371 A1 | 11/2016 | Teetzel et al. | |
| 2017/0176144 A1* | 6/2017 | Zhang | F41G 3/06 |
| 2017/0205202 A1 | 7/2017 | Teetzel et al. | |
| 2017/0286654 A1* | 10/2017 | Nicoll | G06F 21/32 |
| 2018/0106568 A1 | 4/2018 | Hedeen et al. | |
| 2018/0164061 A1* | 6/2018 | Downing | G06K 9/00597 |
| 2018/0224241 A1* | 8/2018 | Havens | F41G 3/142 |
| 2018/0292172 A1* | 10/2018 | Ehrlich | F41G 3/16 |
| 2019/0249958 A1 | 8/2019 | Teetzel et al. | |
| 2019/0330884 A1* | 10/2019 | Reeves | E05B 41/00 |

FOREIGN PATENT DOCUMENTS

| | | |
|---|---|---|
| WO | 20110085464 A1 | 7/2011 |
| WO | 2017127298 A1 | 7/2017 |

OTHER PUBLICATIONS

International Search Report and Written Opinion received in PCT/US2016/030667 dated Jul. 29, 2016.

International Search Report and Written Opinion received in PCT/US2019/035755 dated Aug. 30, 2019.

International Search Report and Written Opinion received in PCT/US2019/018008 dated Apr. 22, 2019.

Extended European Search Report dated Mar. 25, 2022, received in EP19815047.6.

* cited by examiner

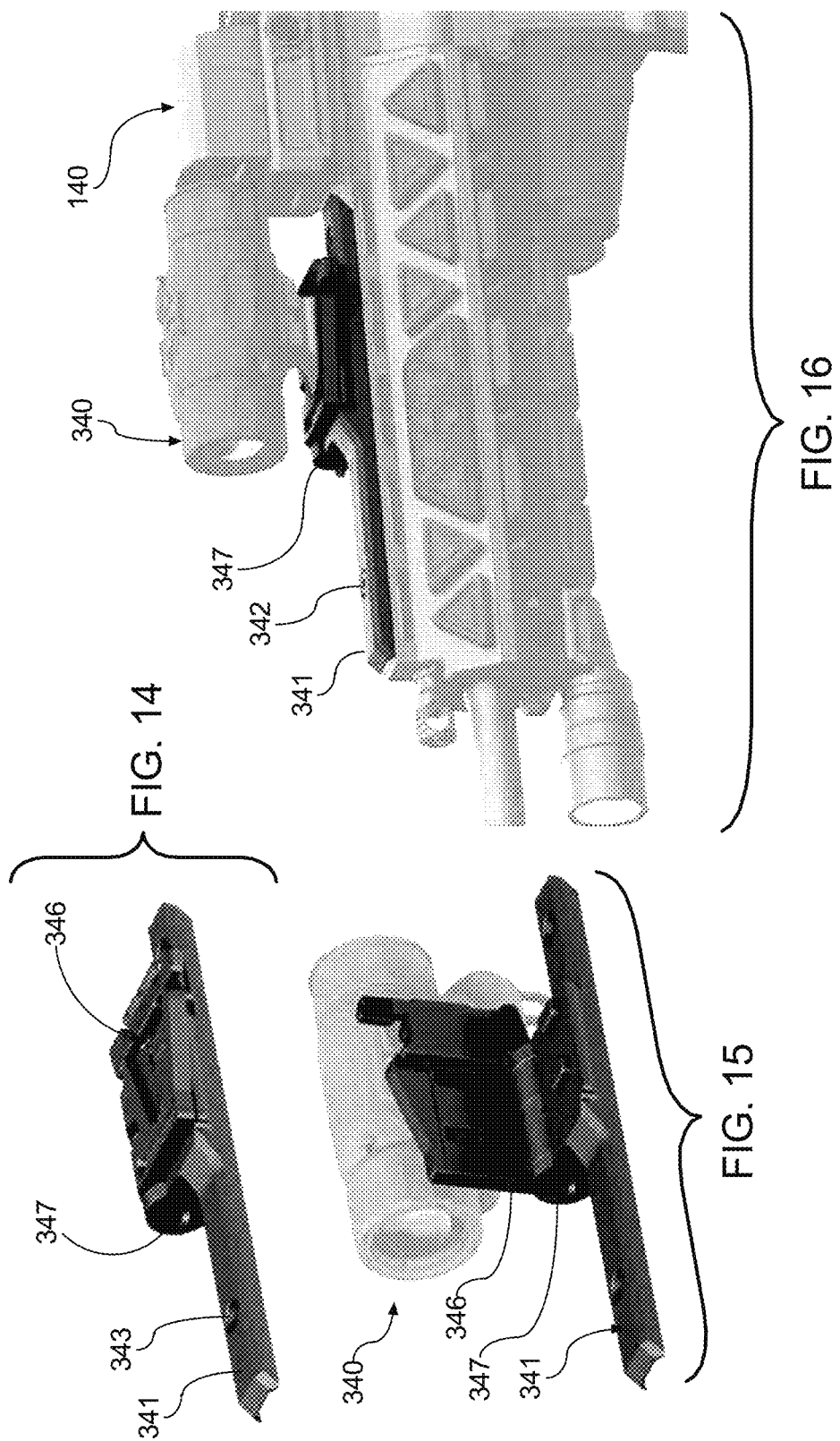

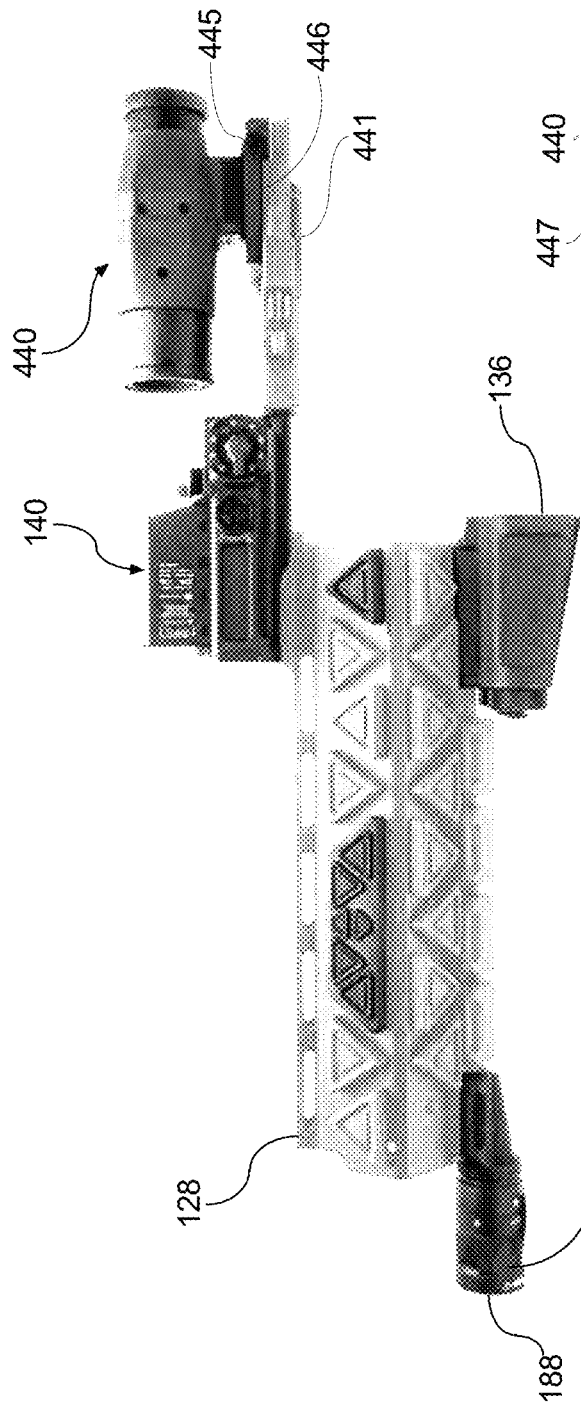
FIG. 17
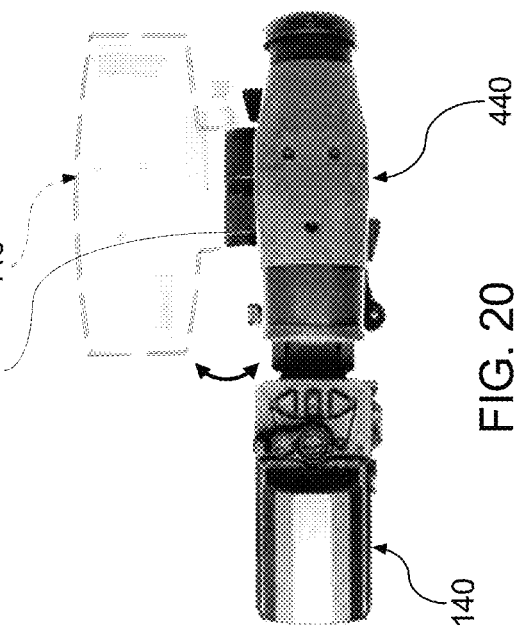
FIG. 20
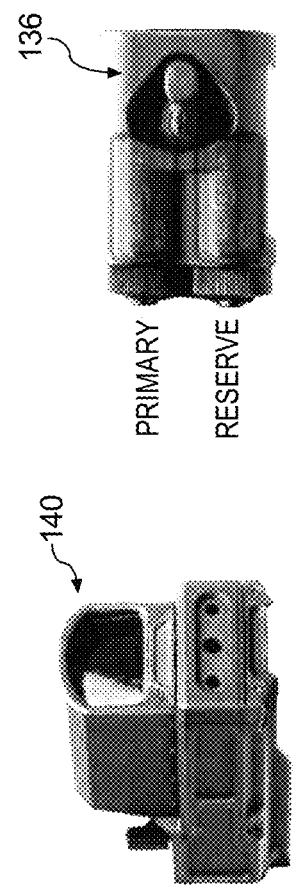
FIG. 19
FIG. 18

Camera (e.g., pin camera) 400 reads bar code 402 embedded in lens of eyewear 412, or, images the users face/retina and uses biometric data (facial recognition or retinal scan data) 408 to identify the user and history of the user (or multiple users) and output to display 176 or output to smart phone 520 display and/or storage media or PDA/mobile computing device 510 display or storage media.

Glove (260) with RFID (260) and eyewear with bar code can be used in combination or individually

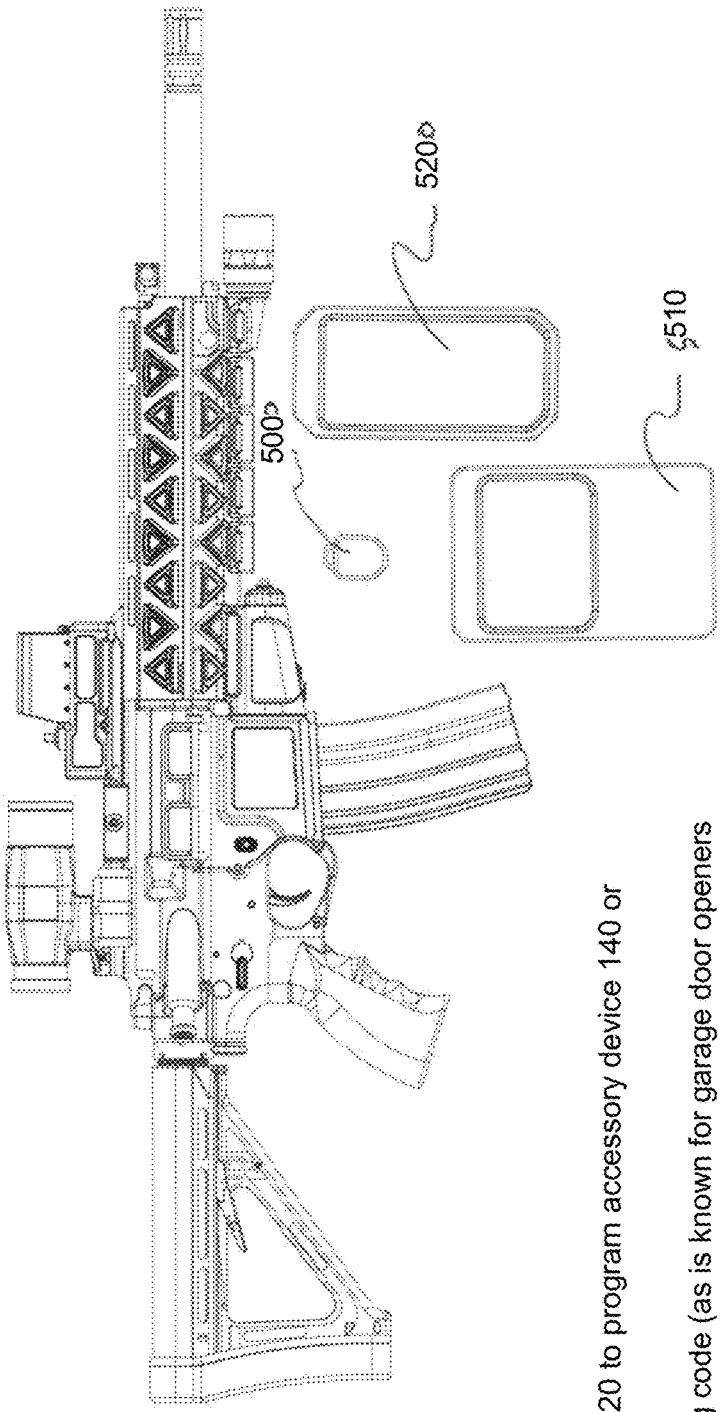

FIG. 24

500, 510, 520 to program accessory device 140 or eyewear

Uses rolling code (as is known for garage door openers or other keyless entry systems) and/or encrypted RF transmission Barcode: Use PDA to scan eyewear and program the memory (407) in the powered rail system or the memory (168) in the accessory device 140

Use 510, 520 to process facial recognition and program accessory device 140 memory 168 and/or the memory 407 in the grip 236

5 METER OPTICAL LRF SWITCH, CQB/OTB AUTO SIGHT ADJUST

GLASSES

BUMP OR BALLISTIC HELMET

STAND ALONE

CUSTOM EAR PIECE IS A DISCRIMINATOR SO AN ENEMY CANNOT FIT IN EAR. ALSO USES UNIQUE BRAIN WAVE BIOMETRIC DATA

RECEIVER UNIQUE GEOMETRY TO ALLOW CONNECTION IN ONLY ONE ORIENTATION

WEAPON SYSTEM WITH OPERATOR IDENTIFICATION

CROSS-REFERENCE TO RELATED APPLICATION

This application claims the priority benefit of U.S. provisional application No. 62/681,486 filed Jun. 6, 2018. The aforementioned application is incorporated herein by reference in its entirety.

INCORPORATION BY REFERENCE

This application is related to U.S. provisional application Ser. No. 62/630,550 filed Feb. 14, 2018 and U.S. non-provisional application Ser. No. 16/275,955 filed Feb. 14, 2019. Each of the aforementioned applications is incorporated herein by reference in its entirety.

SUMMARY

A weapon system for a firearm includes a processor, the processor having an associated memory, and an optical reader, the optical reader configured to receive operator-identification information and transmit the operator-identification information to the processor.

In certain embodiments, the optical reader is a camera configured to generate image signals.

In certain embodiments, the camera is configured to detect optically readable indicia.

In certain embodiments, the optically readable indicia is a bar code.

In certain embodiments, the camera comprises a facial-recognition system responsive to the image signals generated by the camera.

In certain embodiments, the facial recognition system is controllably coupled to the weapon system.

In certain embodiments, the operator-identification information is selected from the group consisting of facial feature data, iris recognition data, eye vein verification data, ocular feature data, machine-readable indicia.

In certain embodiments, the weapons system further includes an accessory eyewear device.

In certain embodiments, the accessory eyewear device comprises a machine-readable indicia.

In certain embodiments, the accessory eyewear device comprises a near-eye display screen.

In certain embodiments, the near-eye display screen is configured to display one or more of the following: a system menu, sighting system menu options, sighting system statistical information, battery power level, user confirmation status, and user biometric data.

In certain embodiments, the machine-readable indicia is selected from the group consisting of: one dimensional bar code, two-dimensional bar code, and Quick Response (QR) code.

In certain embodiments, the camera is capable of reading the machine-readable indicia.

In certain embodiments, the camera is capable of tracking positioning of at least one eye of an operator.

In certain embodiments, the accessory eyewear device further includes an in-ear communication system, the in-ear communication system comprising an electrical connector and an ear-fitting unit removably attachable to the electrical connector.

In certain embodiments, the electrical connector and the ear-fitting unit are removably attachable by a magnetic force.

In certain embodiments, further includes a control unit, the control unit in operable communication with the electrical connector.

In certain embodiments, the ear-fitting unit includes an internal power supply.

In certain embodiments, the ear-fitting unit includes an external power supply.

In certain embodiments, the ear-fitting unit includes an exterior enclosure custom-fitted to a user's ear shape.

In certain embodiments, the ear-fitting unit further includes one or more biological sensors for generating signals representative of biometric information.

In certain embodiments, the biological sensors comprise a means for measuring electrical signals of a user's body.

In certain embodiments, the control unit comprises signal processing circuitry and an audio speaker, wherein the signal processing circuitry is configured to receive the information representative of biometric information and generate an audible notification signal to the audio speaker.

In certain embodiments, the one or more biological sensors are selected from the group consisting of electrodes, temperature transducers, moisture sensors, optical sensors, heart rate sensor, and oxygen saturation sensor.

In certain embodiments, the ear-fitting unit further includes a microphone.

In certain embodiments, the microphone is configured to detect acoustic information representative of a user's acoustic signature.

In certain embodiments, the signal processing circuitry comprises analog-to-digital and digital-to analog conversion circuitry.

In certain embodiments, the control unit further comprises a radio frequency (RF) transceiver.

In certain embodiments, the control unit further comprises a battery power supply.

In certain embodiments, the ear-fitting unit are configured to reduce background noise.

In certain embodiments, the weapon system further includes an external microphone.

In certain embodiments, the signal processing circuitry is configured to generate an audio signal.

In certain embodiments, the audio signal is representative of directional information.

In certain embodiments, the directional information is processed by the signal processing circuitry using sound processing algorithm selected from the group consisting of three-dimensional sound processing algorithm, binaural sound processing algorithm, and head-related transfer function sound processing algorithm.

In certain embodiments, the signal processing circuitry is configured to identify potentially threatening sounds and generate a warning signal.

In certain embodiments, the weapon system further includes an eyewear in operable communication with the ear-fitting unit.

In certain embodiments, the electrical connector is attached to the eyewear.

In certain embodiments, the weapon system further includes a brain computer interface for controlling operation of the weapon system.

In certain embodiments, the weapon system further includes at least one electrode configured to generate brain wave signals, wherein the brain computer interface is configured to monitor and evaluate the brain wave signals.

In certain embodiments, the signal processing circuitry is configured to receive the generated brain wave signals and control operation of the weapon system in response to the generated brain signals.

In certain embodiments, the signal processing circuitry is further configured to generate a weapon system control signal and the RF transceiver is configured to receive the weapon system control signal.

In certain embodiments, the generated brain wave signals are representative of target distance information.

In certain embodiments, the weapons system further includes a pistol grip, the pistol grip housing a safety mechanism in operable communication with the facial recognition system.

In certain embodiments, the weapon system further includes a powered accessory rail interface having an upper accessory rail and a lower accessory rail. A first accessory device is removably attachable to the upper accessory rail and is configured to receive electrical power and data signals over the powered accessory rail interface. A power supply is electrically coupled to the powered accessory rail interface.

In certain embodiment, a second accessory device is removably attachable to the lower accessory rail, the second accessory device configured to receive electrical power and data signals over the powered accessory rail interface.

In certain embodiments, the power supply is a battery box electrically coupled to the lower accessory rail.

In certain embodiments, the weapon system further includes a battery level circuit for determining a charge level of one or more batteries located in the battery box.

In certain embodiments, the weapon system further includes an RF transceiver.

In certain embodiments, the RF transceiver is a Bluetooth transceiver.

In certain embodiments, the weapon system further includes a first RFID reader.

In certain embodiments, the first RFID reader is located in the battery box.

In certain embodiments, the weapon system further includes one or ammunition magazines, each of the one or more ammunition magazines having an RFID chip readable by the RFID reader, the RFID chip configured to transmit information representative of ammunition type to the first RFID reader.

In certain embodiments, the power supply is housed within a pistol grip of the firearm.

In certain embodiments, the weapon system further includes a remote programming fob configured to transmit one or more user program settings to the weapon system via an RF transceiver.

In certain embodiments, the remote programming fob is programmable with one or more of a computer, laptop, and mobile computing device.

In certain embodiments, the weapon system is programmable via the RF transceiver with one or more of a computer, laptop, and mobile computing device.

In certain embodiments, the weapon system further includes a second RFID reader.

In certain embodiments, the weapon system further includes a tactical glove with a RFID chip readable by the second RFID reader, the RFID chip configured to transmit user-identifying information to the second RFID reader.

In certain embodiments, the weapon system further includes a safety mechanism housed within the pistol grip, the safety mechanism configured to prevent operation of the firearm when the tactical glove with RFID chip is not in proximity to the second RFID reader.

In certain embodiments, the safety mechanism includes a plunger and a solenoid configured to selectively lock and unlock a trigger mechanism of the firearm.

In certain embodiments, the pistol grip further comprises a battery level circuit for determining a charge level of one or more batteries located within the pistol grip.

In certain embodiments, the pistol grip includes one or more user input devices for controlling operation of the weapon system, the one or more user input devices selected from the group consisting of one or more buttons, a keypad, a rotary encoder, or any combination thereof.

In certain embodiments, the weapon system further includes one or more sensors on the barrel for sensing one or more of: barrel temperature, barrel strain, a projectile being fired, and a velocity of the projectile.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 14 is an isometric view of the pivot platform.

FIG. 15 is an isometric view of the pivot platform with an accessory device (e.g., camera) attached to the pivot platform and pivoted out of the line of sight.

FIG. 16 is a fragmentary view of the firearm with a second accessory device on the pivot platform in optical alignment with a first accessory device.

FIG. 17 is a fragmentary side view of the weapon system herein with the firearm and pivot platform removed, and further having a third accessory device (e.g., optical scope or magnifier) positioned behind and in optical alignment with the first accessory device (e.g., laser pointer with integral reflex sight).

FIG. 18 is an isometric view of an exemplary accessory device.

FIG. 19 is a bottom view of an exemplary battery box configured to provide electrical power to an accessory device remotely located on the weapon system.

FIG. 20 is a top view illustrating the first and third accessory devices.

FIG. 24 is a side view of the configuration appearing in FIGS. 3 and 4 and further including a programming fob for programming the weapon system in accordance with the user's preferences or custom settings and one or more mobile devices for programming the fob and/or for programming the weapon system directly.

DETAILED DESCRIPTION OF THE PREFERRED EMBODIMENTS

Figure 1:
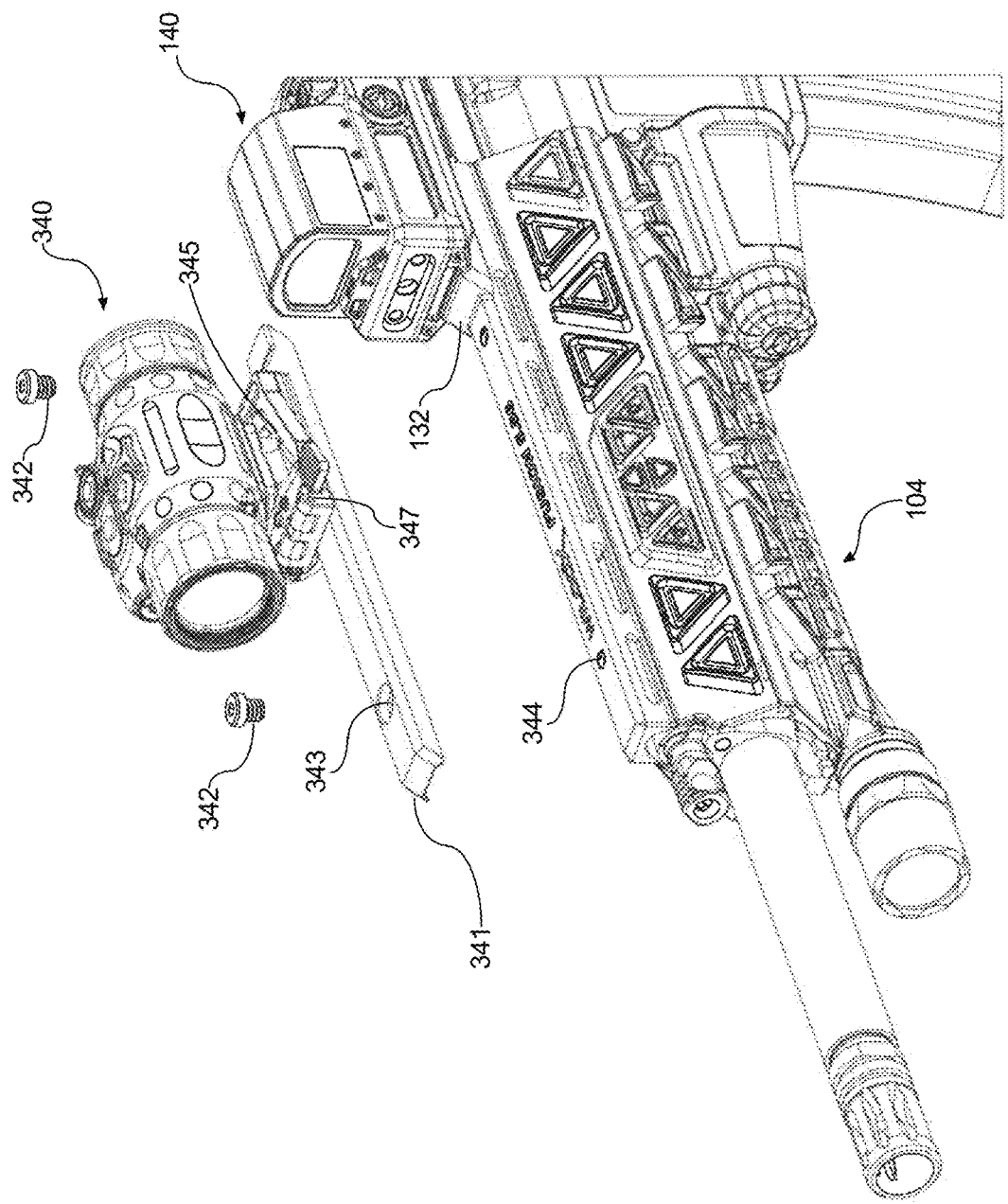
FIG. 1 is an isometric, partially exploded fragmentary view of an exemplary weapon system in a configuration having first and second accessory devices.
Figure 2:
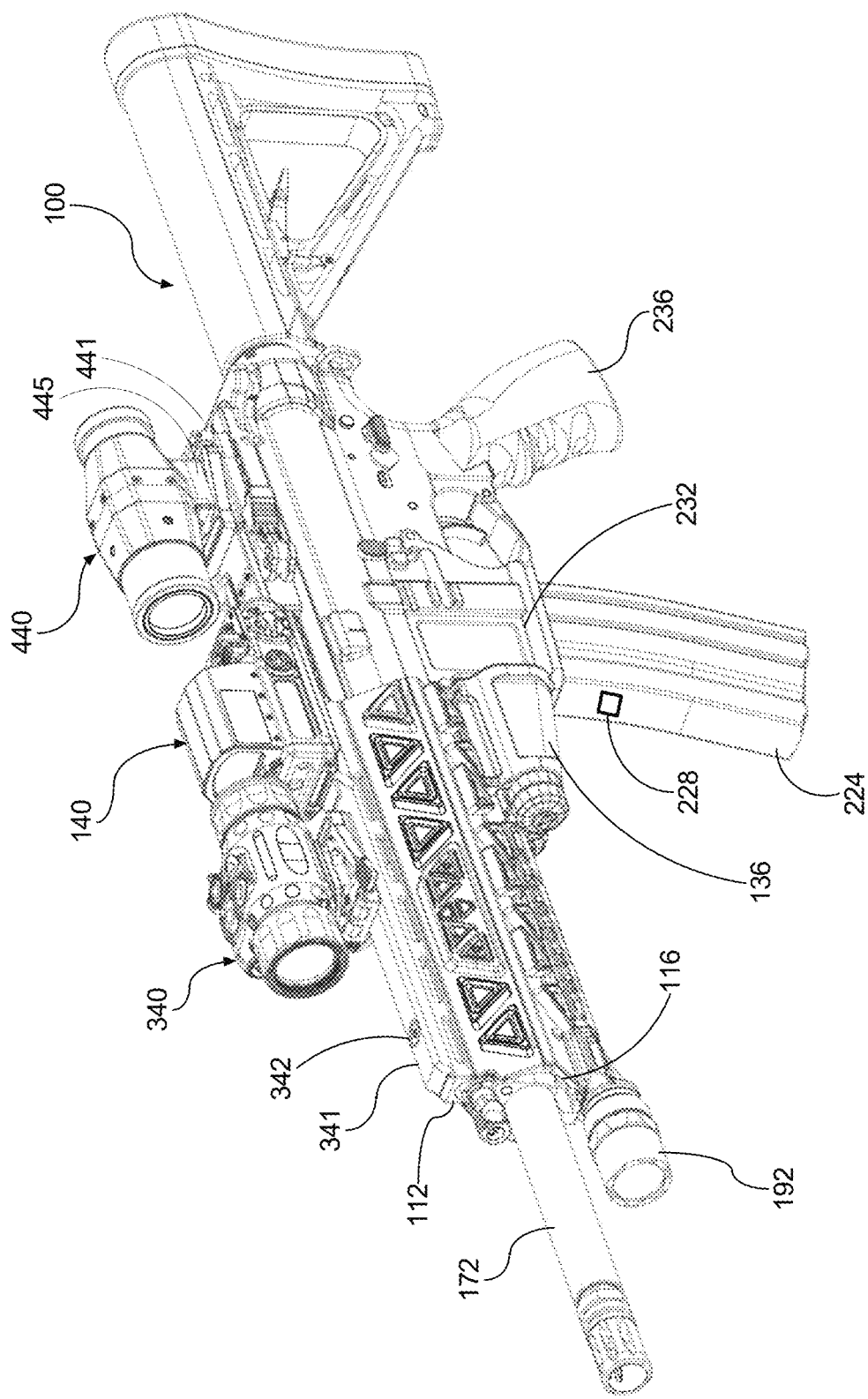
FIG. 2 is an isometric view of the weapon system appearing in FIG. 1, including the first and second accessory devices, and further including an optical scope or magnifier.
Figure 3:
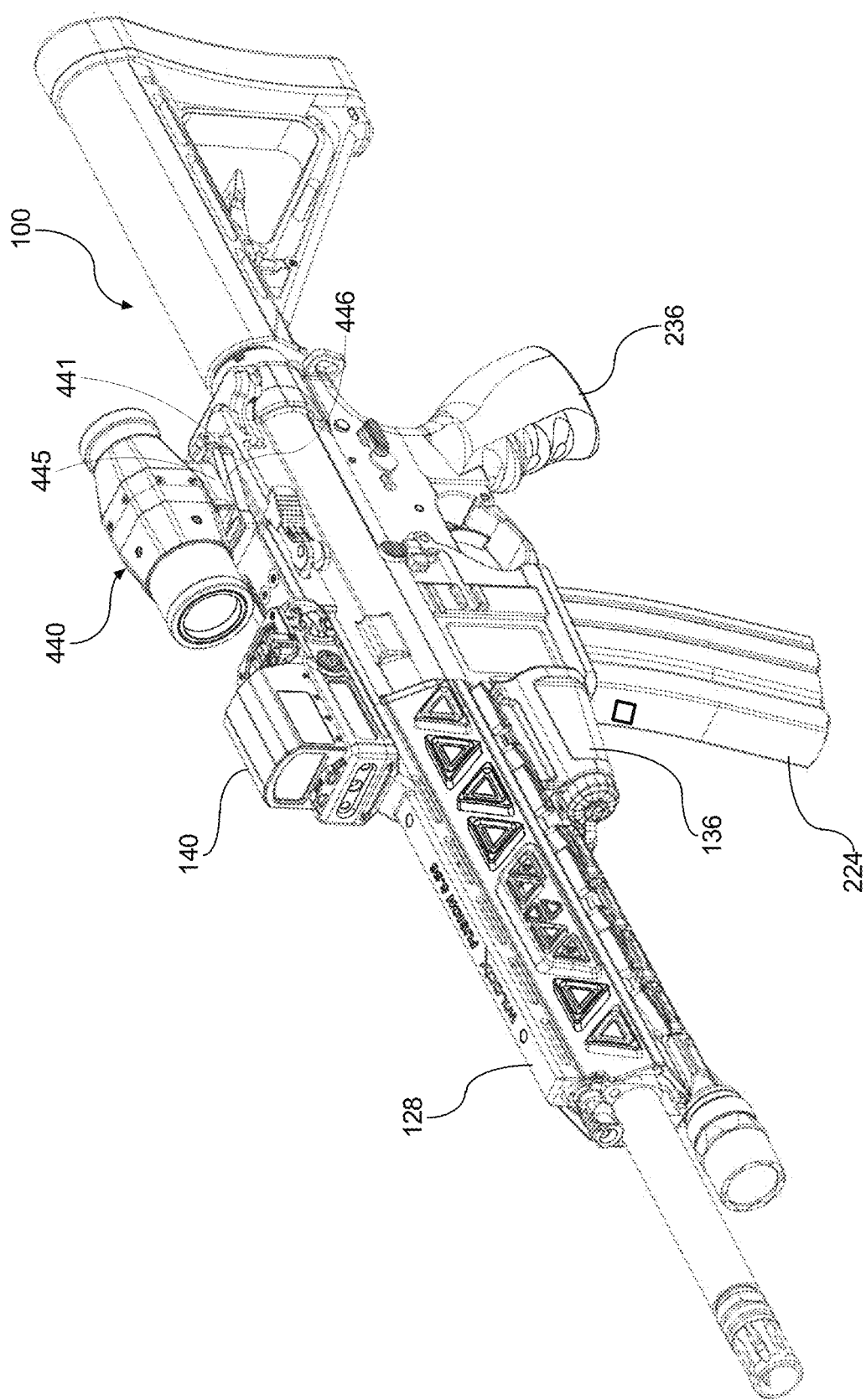
FIG. 3 is an isometric view of the weapon system appearing in FIG. 1, including the first accessory device and the optical scope or magnifier.

Referring now to the drawings, wherein like reference numerals are used to denote like components throughout the several views, the present development relates to a weapon system for use in connection with a weapon such as a firearm 100 and includes a powered accessory rail or platform 104.

In certain embodiments, the powered accessory platform 104 includes a handguard assembly 108 including an upper handguard portion 112 and an opposed lower handguard portion 116, wherein the upper handguard portion 112 and the lower handguard portion 116 cooperate to define a sleeve, the sleeve having a proximal end configured to attach to the weapon 100 and a distal end opposite the proximal end. The weapon system is configured to sense, receive, and process data to adjust and compensate for weapon performance, for example, to compensate for barrel whip, temperature, harmonic characteristics, etc.

The handguard assembly 108 is configured to surround at least a portion of the weapon 100 when the proximal end is attached to the weapon. An electrical circuit 126 is disposed within the sleeve defined by the handguard assembly 108. In certain embodiments, the electrical circuit 126 includes a flexible circuit comprising one or more circuit elements, including printed circuit elements, disposed on a flexible circuit substrate. In certain embodiments, the electrical circuit is configured to electrically couple one or more electrically operated devices to a power supply and to provide a data and control signal interface between attached units. A suitable electrical circuit 126 is disclosed in commonly owned U.S. Patent Application Publication No. US2017/0205202 published Jul. 20, 2017 (Ser. No. 15/404,505 filed Jan. 12, 2017), which is incorporated herein by reference in its entirety.

In certain embodiments, an accessory mounting rail 128 is located on a top portion of the upper handguard portion 112, the mounting rail 128 having at least one electrical connector thereon. In certain embodiments, an accessory mounting pad 132 is mechanically and electrically coupled to the accessory mounting rail 128 and electrically couples to a power supply 136 removably attached to the accessory platform 104. An accessory device 140 is mechanically and electrically coupled to the accessory mounting pad 132.

In certain embodiments, the powered accessory rail or platform 104 may be of the type disclosed in commonly owned U.S. Patent Application Publication No. US2016/0327371 published Nov. 10, 2016 (Ser. No. 15/146,094 filed May 4, 2016), which is incorporated herein by reference in its entirety, or the aforementioned commonly owned U.S. Patent Application Publication No. US2017/0205202.

The accessory device 140 is removably attachable to the accessory mounting pad 132 on the accessory platform 104. In certain embodiments, the accessory device 140 is a laser sight. In certain embodiments, the laser sight includes multiple lasers. In certain embodiments, the laser sight includes an integral reflex sight. In certain embodiments, the laser module may be of the type disclosed in commonly owned U.S. Patent Application Publication No. US2016/0102943 published Apr. 14, 2016 (Ser. No. 14/881,779 filed Oct. 13, 2015), which is incorporated herein by reference in its entirety.

In certain embodiments, a second accessory device 340 is removably attached to a pivot platform 341 which is located on the accessory mounting rail 128. In certain embodiments, the pivot platform 341 is removably attached to the accessory mounting rail by means of one or more threaded screws 342, which are threaded through one or more threaded openings 343 in the pivot platform 341, corresponding with one or more threaded openings 344 in the accessory mounting rail 128. The second accessory device 340 may be a camera, such as a thermal camera, complementary metal-oxide-semiconductor (CMOS) image sensor, or short wave infrared camera (SWIR), although other accessory devices are contemplated. The second accessory device 340 includes a dovetail mounting shoe 345 configured to be received in a mounting shoe receiver 346 of the pivot platform. In certain embodiments, the pivot platform is mechanically and electrically coupled to the accessory mounting rail 128 and power supply 136.

The pivot platform includes a pivot or hinge mechanism 347 which allows the second accessory device 340 to be pivotally adjusted from a first position substantially on top of the pivot platform to a second position substantially to the side of the pivot platform. In certain embodiments, when the second accessory device 340 is in the first position, the second accessory device 340 is coaligned with the first accessory device 140 such that the first and second accessory devices may be used together in single operation. In certain embodiments, the pivot platform includes a lock or clamp device holding the second accessory device 340 in place in the first position. A release mechanism is included such that activation of the release allows the second accessory device 340 to be movable to a second or stowed position. In certain embodiments, when the second accessory device is moved from the second, stowed position to the first, operative position, the second accessory device 340 receives power from power supply 136. In certain further embodiments, a switch is provided, such that, when the second accessory device 340 is moved from the first, operative position to the second, stowed position, the second accessory device does not receive power from power supply 136. The switch may be a mechanical switch or a proximity switch, e.g., employing a magnet element and a proximity sensor such as a magnetic reed switch or a Hall effect sensor.

In certain preferred embodiments, the laser sight includes a laser module 144 having one or more lasers, including for example, a visible target pointer laser 148, an infrared (IR) target pointer laser 152, and an IR illuminator or flood light laser 156. In certain embodiments, the lasers 148, 152, and 156 are factory co-aligned on an optical bench and potted with a potting compound during manufacture to maintain the co-aligned state.

In certain embodiments, the accessory device 140 further includes an integrated reflex sight 160. In certain embodiments, the reflex sight 160 is co-aligned with the laser module 144.

In certain embodiments, the accessory device 140 includes a processor 164 and an associated electronic memory 168. In certain embodiments, the memory 168 includes a program of instructions executed by the processor 164 for performing ballistics calculations based on, e.g., distance to a target, ammunition type, and other factors, by automatically adjusting the sight to assist the user in aligning the barrel 172 of the weapon 100 to achieve a firing trajectory which will cause the path of a projectile fired by the weapon 100 to intersect with the position of a desired target. In certain embodiments, the firing trajectory is adjusted based on the processor's calculations, via a stepper motor and a wedge. The stepper motor selectively advances or retracts a wedge that changes the bias of the laser bench, thereby adjusting the angle of the sight trajectory. One stepper motor/wedge may be provided to provide an elevation adjustment and another stepper motor/wedge may be provided to provide a lateral (windage) adjustment.

In certain embodiments, the trajectory is automatically adjusted based on one or both of (a) the type of ammunition installed; and (b) the distance detected with a range finder component as will be described below.

In certain embodiments, the memory 168 includes a program of instructions executed by the processor 164 for calculating barrel performance.

In certain embodiments, the memory 168 includes a program of instructions executed by the processor 164 for calculating barrel whip.

In certain embodiments, the accessory device 140 includes a human-viewable display 176, such as an LCD display, LED display, etc., and associated display driver electronics, operably coupled to the processor 164.

The processor 164 is configured to receive data or signals representative of one or more system parameters, which are logged and stored in the memory 168. In certain embodiments, the system parameters may be any one or more of the following:

1. Round count based on barrel sensor output (described below),

2. Barrel temperature based on barrel sensor (thermocouple) output.

3. Barrel mileage/life expectancy based on barrel sensor output

4. Rate of fire, e.g., measured in rounds per minute (RPM), based on barrel sensor output.

5. Bullet velocity based on barrel sensor output.

6. Laser mode, e.g., visible, IR, IR Flood, IR+IR Flood.

7. Ammunition cartridge type, including: training rounds (e.g., blanks or non-lethal ammunition rounds), low velocity rounds (e.g., 300 AAC Blackout subsonic rounds), high velocity rounds (e.g., 300 AAC Blackout supersonic rounds), and so forth, based on a radio frequency identification (RFID) tag associated with an installed ammunition magazine.

8. Cant/Tilt function based on an orientation sensor 180, which may be, e.g., an accelerometer, inclinometer, or the like. A visual indication of the degree of firearm cant or tilt may be output to the display 176 to assist the shooter in leveling the firearm 100 or be used to determine the direction in which the firearm is pointed. For example, aiming direction information may be used in cooperation a gun lock mechanism, the orientation sensor 180 may be used as an active friend-or-foe system.

9. Battery power remaining (state of charge), e.g., based on output signal from a battery consumption or monitoring circuit 184, such as a Coulomb counter, battery fuel gauge integrated circuit, voltmeter for measuring battery output voltage or voltage drop due to battery internal resistance, and the like. In certain embodiments, battery state of charge information is stored in a battery power database 320 in the memory 168. A visual indication of the battery life remaining, e.g., as a percentage based on an estimated battery life, may be output to the display 176.

Figure 4:
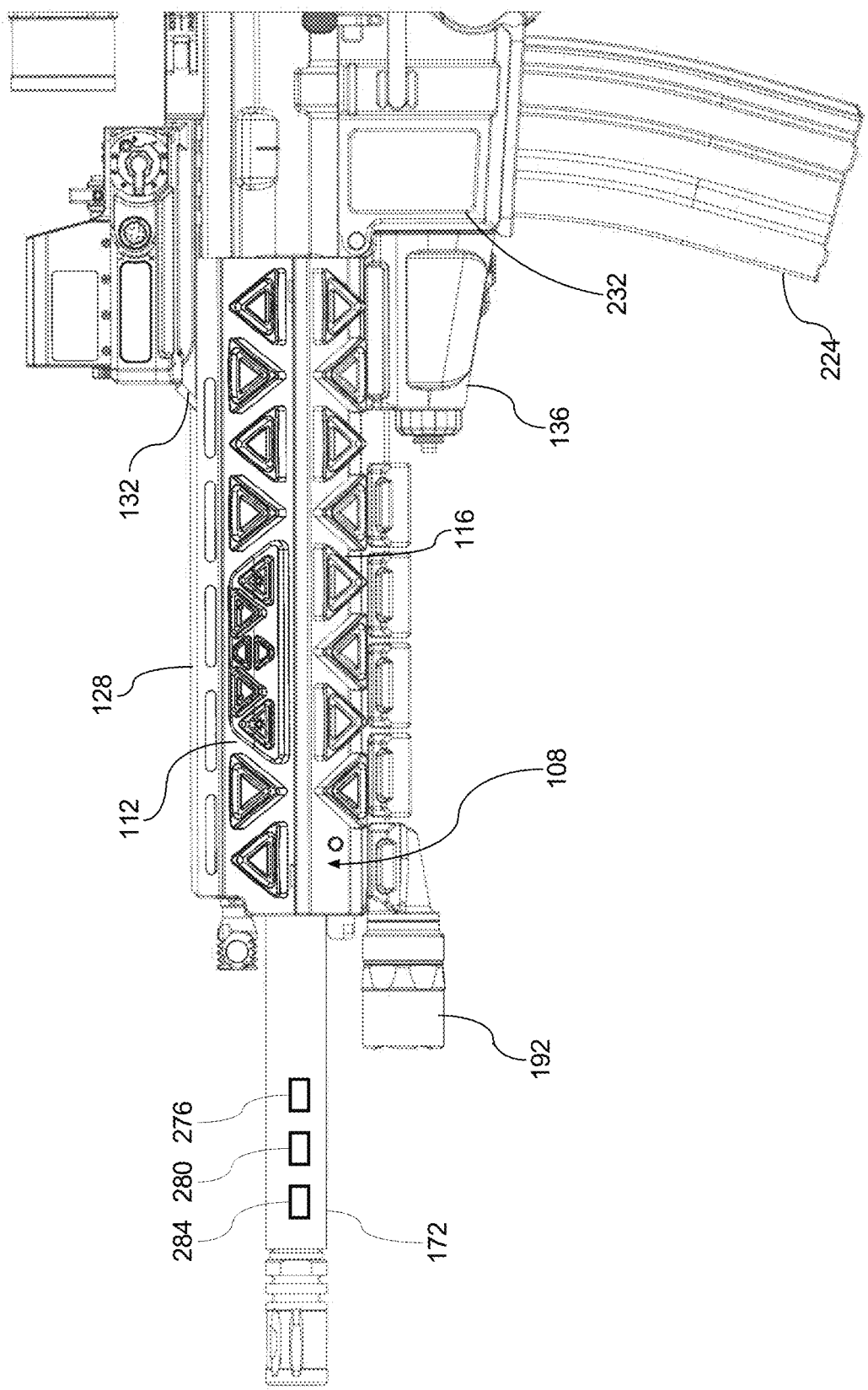
FIG. 4 is a fragmentary side view of the weapon system configuration appearing in FIG. 3.
Figure 5:
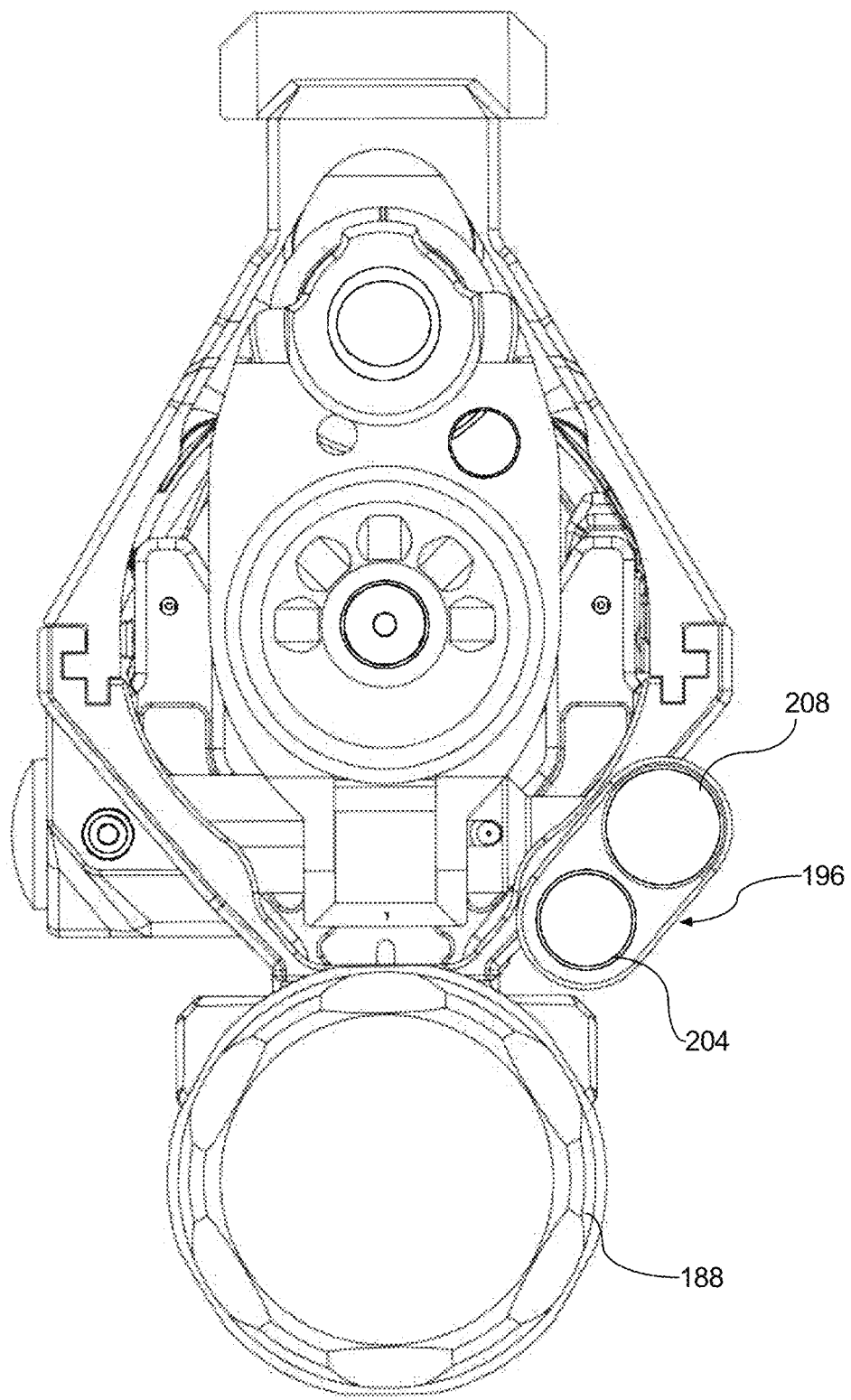
FIG. 5 is a front elevation view of the fore end portion of the illustrated weapon system.
Figure 6:
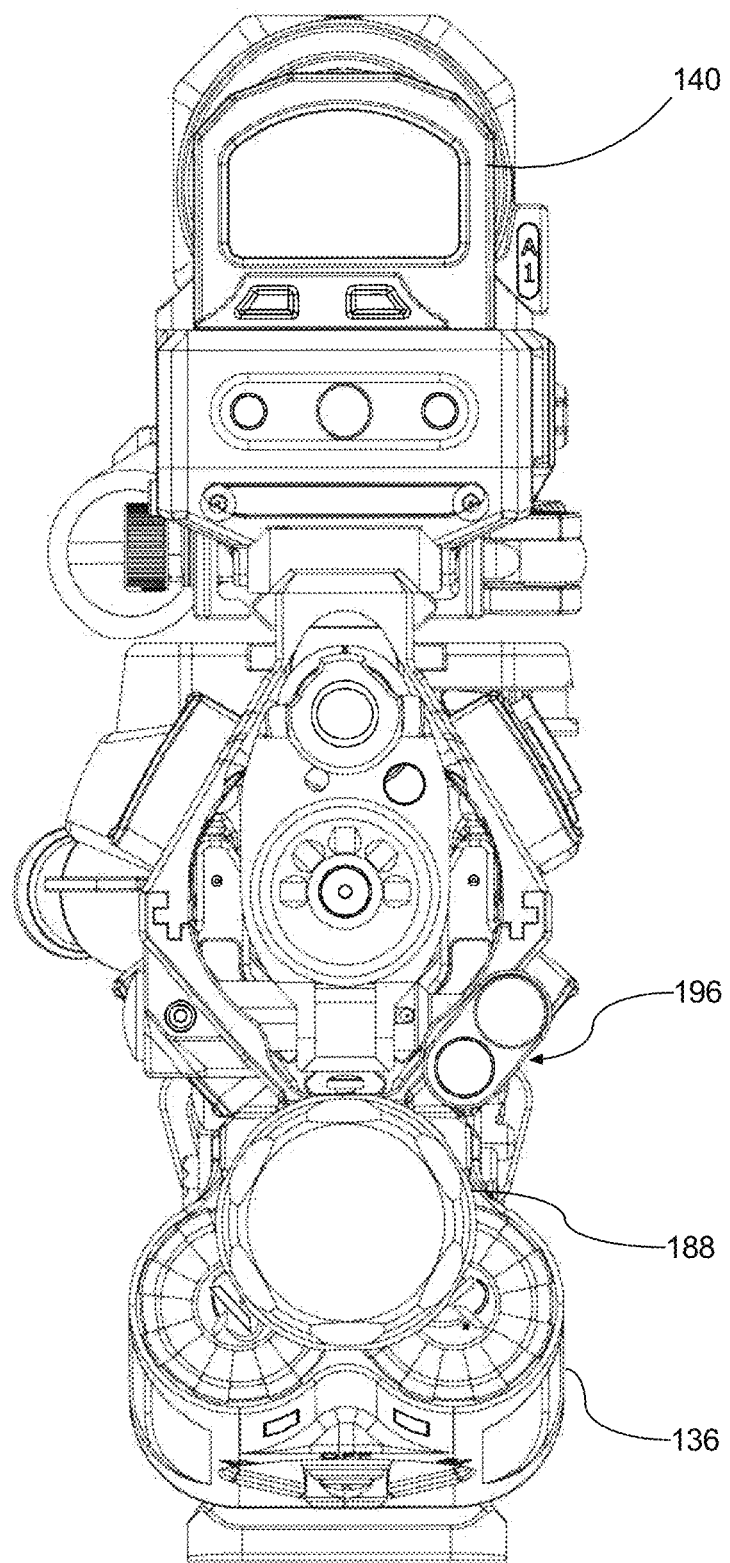
FIG. 6 is a front elevation view of the weapon system configuration appearing in FIGS. 3 and 4 with the magazine removed.
Figure 7:
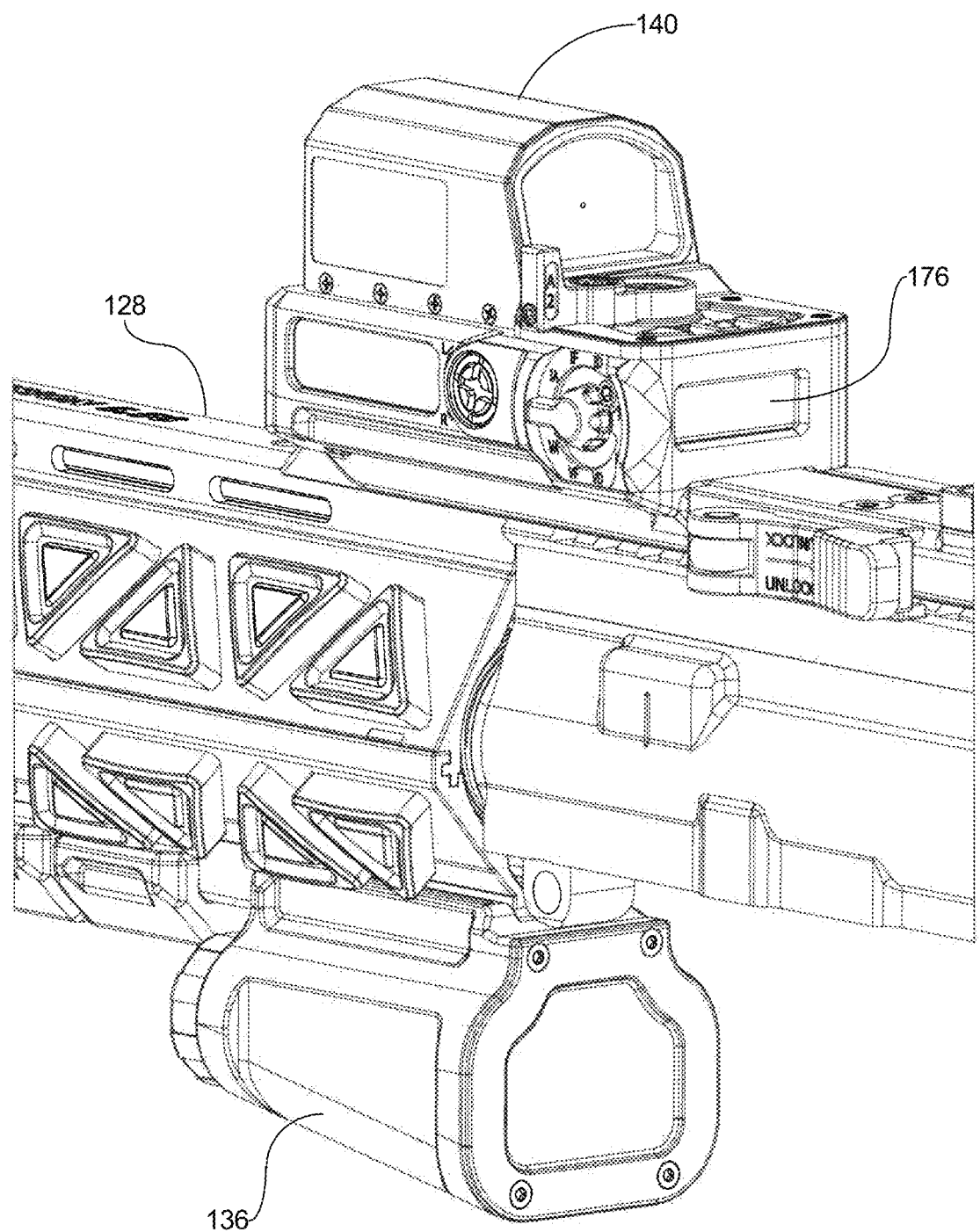
FIG. 7 is a fragmentary isometric view taken generally from the rear and left side.

10. Barrel whip based on barrel sensor output and barrel harmonic characteristics associated with ammunition cartridge type, barrel length, temperature, and the like. In certain embodiments, barrel information is logged in a barrel whip database 328 stored in the memory 168. With reference to FIG. 4, bullet/projectile placement varies as a function of (1) the position/alignment of the barrel in relation to the sight that is used to aim the weapon and (2) barrel whip and in particular, the location of the last 120 mm of the barrel as the bullet/projectile exits the barrel. Barrel whip characteristics change as a function of barrel conditions. For example, as the barrel heats up, the barrel droops more, thereby changing the position of the barrel. Shooting the weapon also changes the barrel position. One or more strain gauges monitor such barrel conditions.

11. Distance to target, which may be obtained from a range finder, e.g., an optical range finder integral with the accessory device 140 (not shown) or a separate range finder associated with the weapon system and in communication with the weapon system herein which communication may be via a wired or wireless communication interface. In certain embodiments, the distance to target is logged in a database 324 stored in the memory 168 and may be selectively displayed as an item of information on the display 176.

In certain embodiments, the distance to target is determined using a rangefinder 196 associated with a flashlight module 188. The flashlight module 188 is attached at the distal end of the lower handguard member and is electrically coupled to the power supply 136 via the circuit 126. The flashlight module includes a flashlight head portion 192 and an optical range finder 196. A mounting member 200 provides a removable electrical and mechanical connection to the lower handguard member 116.

The flashlight head 192 includes one or more light emitting elements, preferably LEDs. In certain embodiments, the flashlight head 192 includes one or more LEDs which emit radiation in a visible portion of the electromagnetic spectrum. In other embodiments, the flashlight head 192 includes one or more LEDs which emit radiation in an infrared portion of the electromagnetic spectrum. In still further embodiments, the flashlight head 192 is a dual mode flashlight which includes one or more LEDs for selectively emitting radiation in a visible portion of the electromagnetic spectrum and one or more LEDs for selectively emitting radiation in an infrared portion of the electromagnetic spectrum.

In certain embodiments, the range finder 196 comprises a laser emitter 204 and an optical sensor or receiver 208. The laser 204 sends a beam toward an intended target and reflections of the beam from the target object are detected by the optical receiver 208. The distance to the target is calculated based on the time-of-flight of the laser beam. In certain embodiments, the laser 204 emits a laser beam in a very short series of pulses, which may be encoded to assist the detector 208 in recognizing the reflected signal.

In certain embodiments, range finder 196 operates as an optical switch to automatically adjust the trajectory of the sight 140 between a "Close Quarter Battle" (CQB) setting and an "Over the Beach" (OTB) setting, under programmed control of the processor 164, depending on whether the target is within some predetermined threshold value, e.g., some value between 5 and 20 meters, preferably between 5-10 meters, most preferably 10 meters. In certain embodiments, if the trajectory of the sight is set in the OTB setting and the range finder 196 detects that the target is within such predetermined distance, the trajectory of the sight is adjusted to the CQB setting. In certain embodiments, if the trajectory of the sight is set in the CQB setting and the range finder 196 detects that the target is at a distance greater than the predetermined distance, the trajectory of the sight is adjusted to the OTB setting.

Power may be supplied to the accessory device(s) 140 and 240, flashlight module 188, or other attached electrically operated devices by one or more of an internal or dedicated power supply for each device, or alternatively or additionally, one or both of the battery box 136 attached to the accessory platform 104 and a power supply 123 contained within a pistol grip 236. In certain embodiments, the power supply 136 is a battery box as described in the aforementioned commonly owned U.S. Patent Application Publication No. US2017/0205202.

The power supply(ies) includes one or more batteries. In certain embodiments, the power supply includes an RFID reader. In certain embodiments, the power supply 136 includes an RF transceiver interface, such as a Bluetooth transceiver 222. In certain embodiments, the handgrip 236 includes an RF transceiver interface, such as a Bluetooth transceiver 253.

In certain embodiments, a third accessory device 440 is removably attached to an ear pivot platform accessory mount, 441, which is located on the firearm upper receiver behind the pivot platform 341. In certain embodiments, the rear pivot platform 441 is removably attached to the firearm upper receiver by means of one or more threaded fasteners (not shown), which engage one or more aligned threaded openings rear pivot platform 441 and a corresponding one or more threaded openings in the firearm upper receiver. The third accessory device 440 may be an optical device such as an optical magnifier or optical scope. In certain embodiments, the third accessory device 440 is an optical magnifier, e.g., a 3× or 4× optical magnifier, to provide an enlarged view of the integrated reflex sight. The third accessory device 440 includes a dovetail mounting shoe 445 configured to be received in a mounting shoe receiver 446 of the rear pivot platform 441. In certain embodiments, the rear pivot platform is mechanically and electrically coupled to the accessory mounting rail 128 and power supply 136.

The rear pivot platform includes a pivot or hinge mechanism 447, which allows the third accessory device 440 to be pivotally adjusted from a first position in optical alignment with the first accessory device 140 wherein to a second position wherein the third accessory device 440 is moved out of optical alignment with the first accessory device 140. In certain embodiments, when the third accessory device 340 is in the first position, the third accessory device 440 is coaligned with the first accessory device 140 such that the first and second accessory devices may be used together in single operation. Similarly, in certain embodiments wherein both the second accessory device 340 and the third accessory device 440 are attached and in their respective first or operative positions, the first, second, and third accessory devices (140, 340, 440) are coaligned with the first accessory device 140 such that the first, second and third accessory devices may be used together in single operation.

In certain embodiments, the pivot platform includes a lock or clamp device holding the third accessory device 440 in place in the first position. A release mechanism is included such that activation of the release allows the third accessory device 440 to be movable to the second, stowed position.

Figure 12:
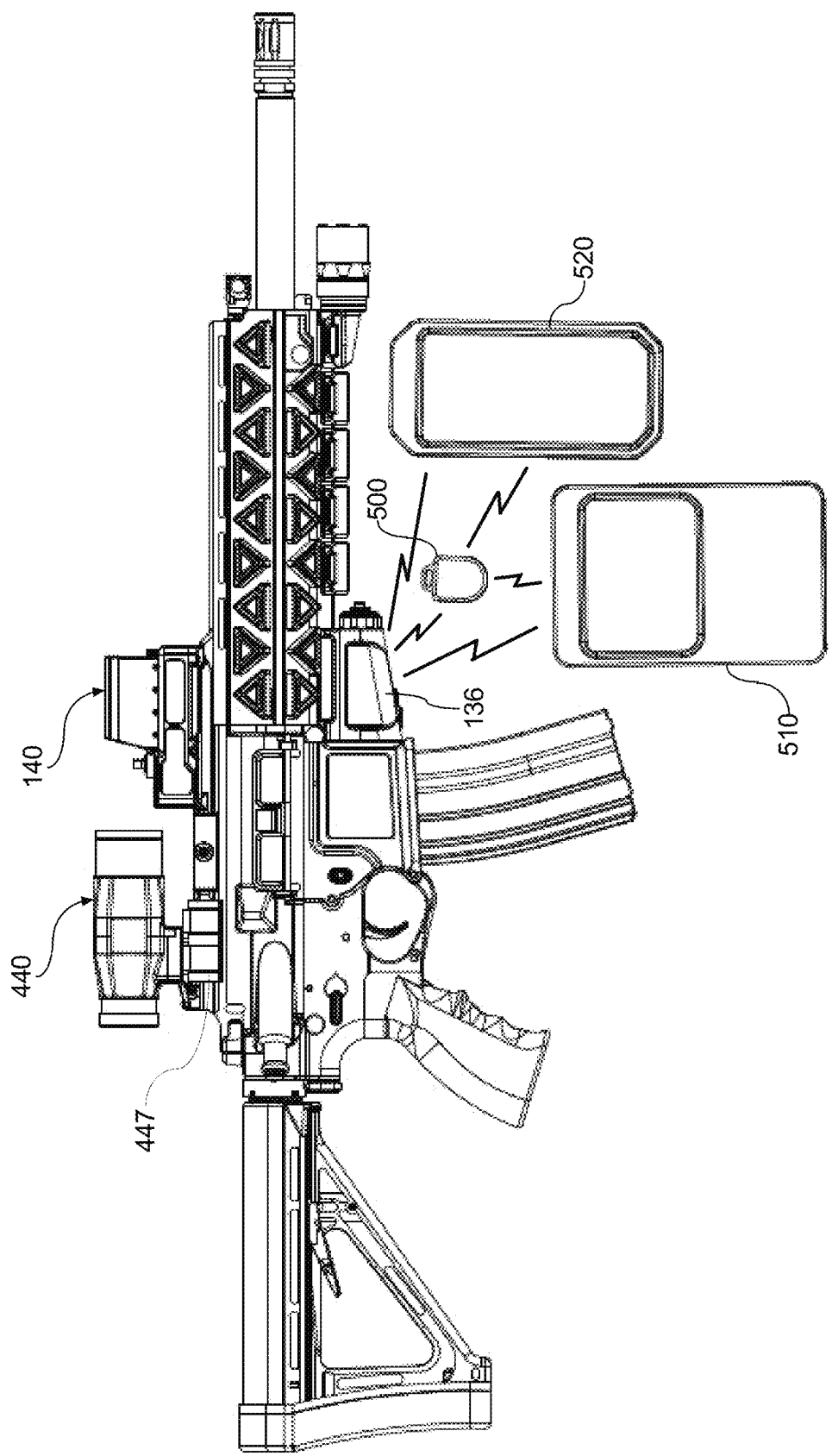
FIG. 12 is a side view of the configuration appearing in FIGS. 3 and 4 and further including a programming fob for programming the weapon system in accordance with the user's preferences or custom settings and one or more mobile devices for programming the fob and/or for programming the weapon system directly.
Figure 13:
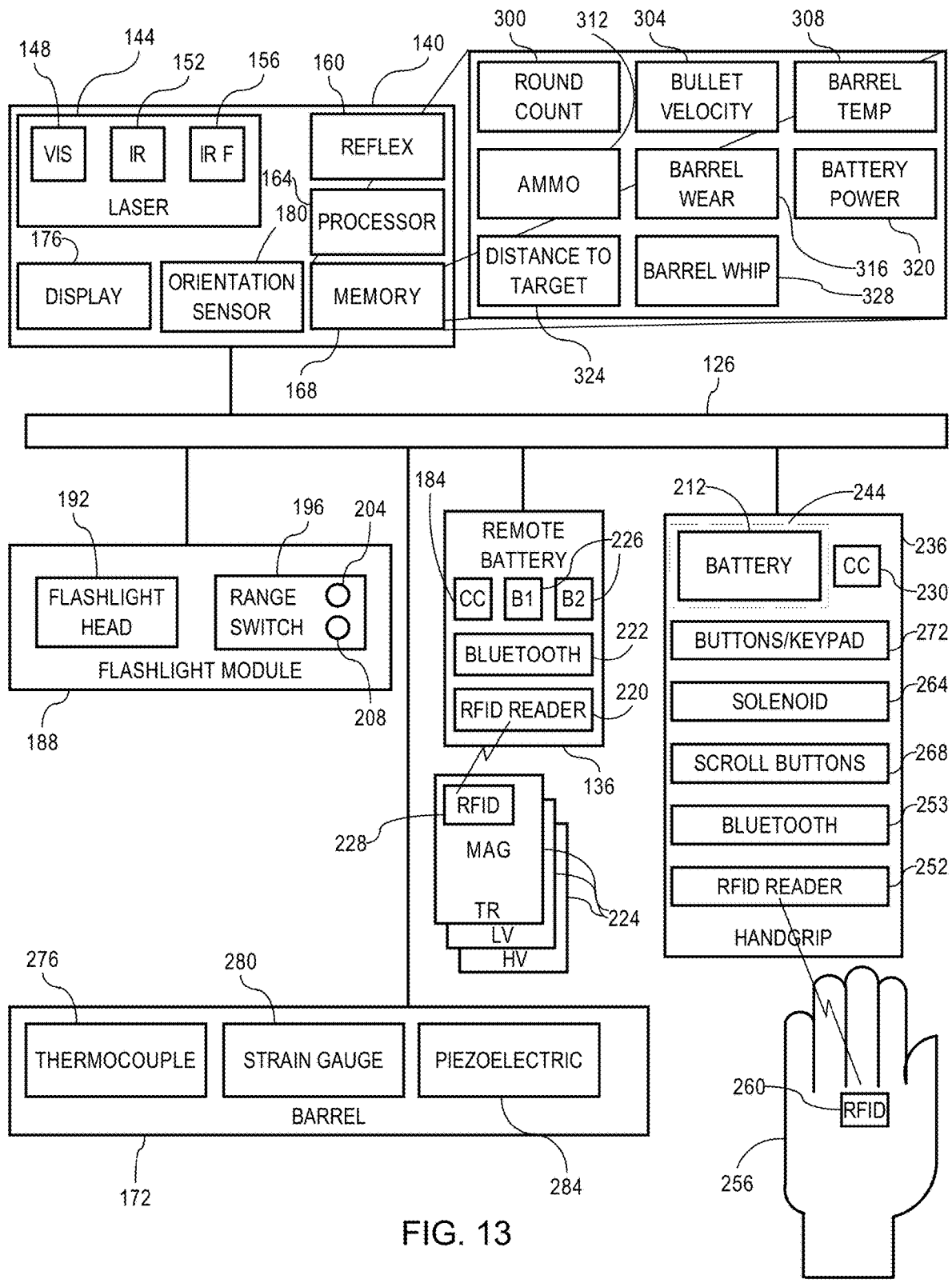
FIG. 13 is a block diagram illustrating an exemplary weapon system in accordance with the present disclosure.
Figure 21:
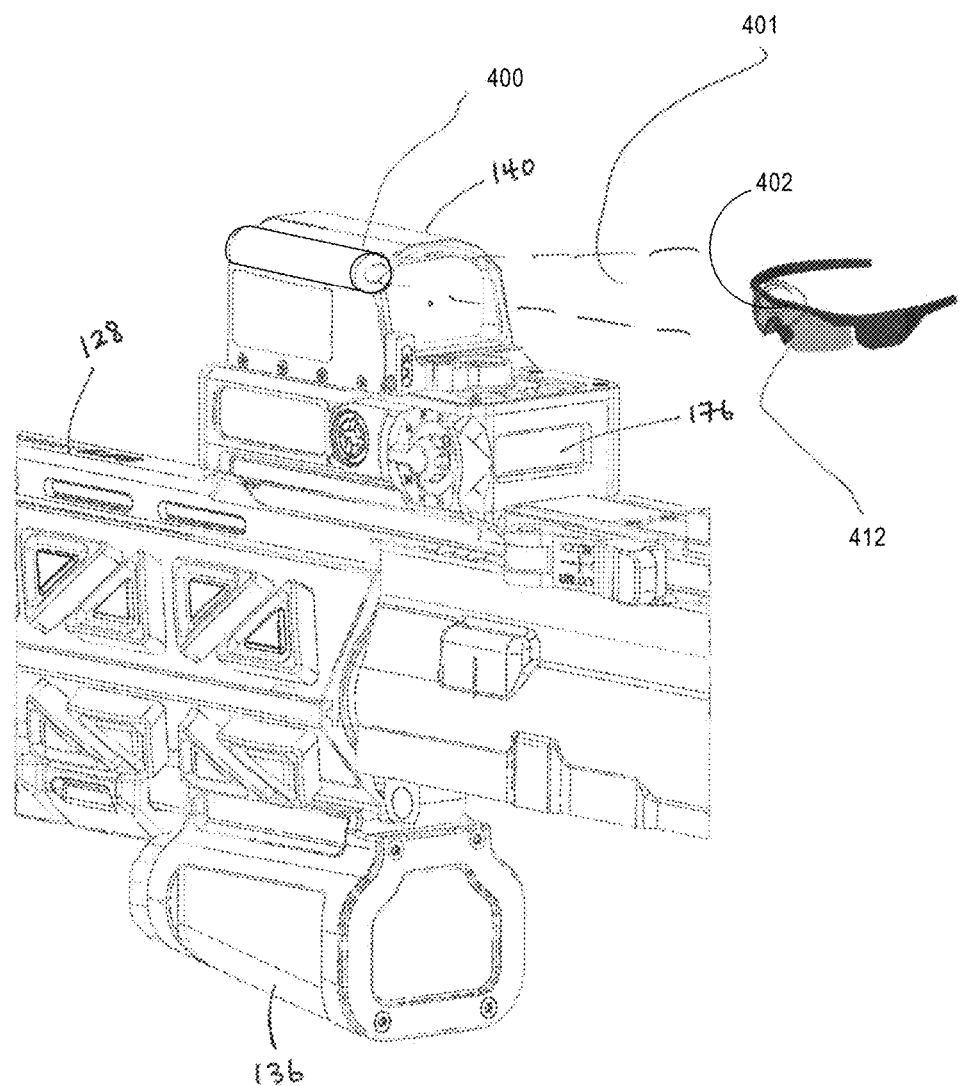
FIG. 21 is a fragmentary isometric view of the configuration appearing in FIGS. and 4 and further including an accessory eyewear device.

As illustrated in FIG. 12, certain embodiments of the weapon system includes a fob, e.g. key chain type fob, or other portable associated device 500, that is programmable to store user customizable device settings. This avoids the need for the user have to take the time to go through all the programming steps to customize it to the person. For example, a soldier may pick up another soldier's rifle that has different settings, and quickly change it over to his or her settings. Thus, the soldier only needs to worry about picking up a gun and shooting it without the confusion or delay of programming. The cell phone or other mobile device, through an app, can do the programming off line, and then transfer it to the battery box controller, either directly or through a programmable key fob.

The fob 500 includes an RF transceiver interface, such as a Bluetooth transceiver. The fob 500 may be remotely and wirelessly programmed, for example, through a fob programming unit, which may be a dedicated fob programming device 510 or a mobile device such as a cell phone, smart phone, handheld data terminal, etc., to configure and store desired weapon systems settings. The battery box 136 includes a transceiver which is capable of receiving a radio frequency signal emitted by the pre-programmed fob 500.

When brought within range of the battery box, the preprogrammed fob 500 transmits the stored custom user settings from the fob 500 to the weapon system and programs the weapon system with the desired settings. In certain embodiments, the fob 500 includes an actuator button for transmitting the settings to the battery box transceiver. In certain embodiments, as an alternative to using the fob 500, the programming device 510 or alternatively the cell phone, smart phone, or hand held data terminal 520, etc. running an application program, is programmed user and is then used to transmit the custom program information or settings directly via the Bluetooth transceiver in the battery box without the fob 500.

In certain embodiments, multiple interchangeable magazines 224 configured for holding different types of ammunition cartridges are provided. In certain embodiments, each magazine 224 has an RFID tag 228 attached thereto. The RF tag 228 may be active, semi-active, or passive and contains stored data representative of the type of ammunition cartridges stored within the magazine 224. In the illustrated embodiment, the RFID reader 220 in the battery box 136 sends signals to and receives signals from the RFID tag 228. However, it will be recognized that the associated RFID reader may be disposed elsewhere, such as on the firearm upper or lower receiver or on the accessory platform 104 or other device attached to the firearm.

The RF reader 220 and RFID tag 228 are capable of sending and receiving electromagnetic signals to and from each other, thereby allowing the reader to interrogate the tag 228 and obtain data representative of the type of ammunition rounds stored in the magazine that is currently inserted into the magazine well 232 of the firearm 100. In certain embodiments, the RFID tag 228 is a passive RF tag which does initiate communications with the RFID reader 220, but must be read, i.e., wherein the RFID tag 228 utilizes power from the RF waves transmitted by the RFID reader 220. In preferred embodiments, the communication range between the RFID reader 220 and the RFID tag 228 is in the range of 0 to 1 meter, preferably 0 to 30 centimeters, and more preferably 0 to 20 centimeters.

Figure 8:
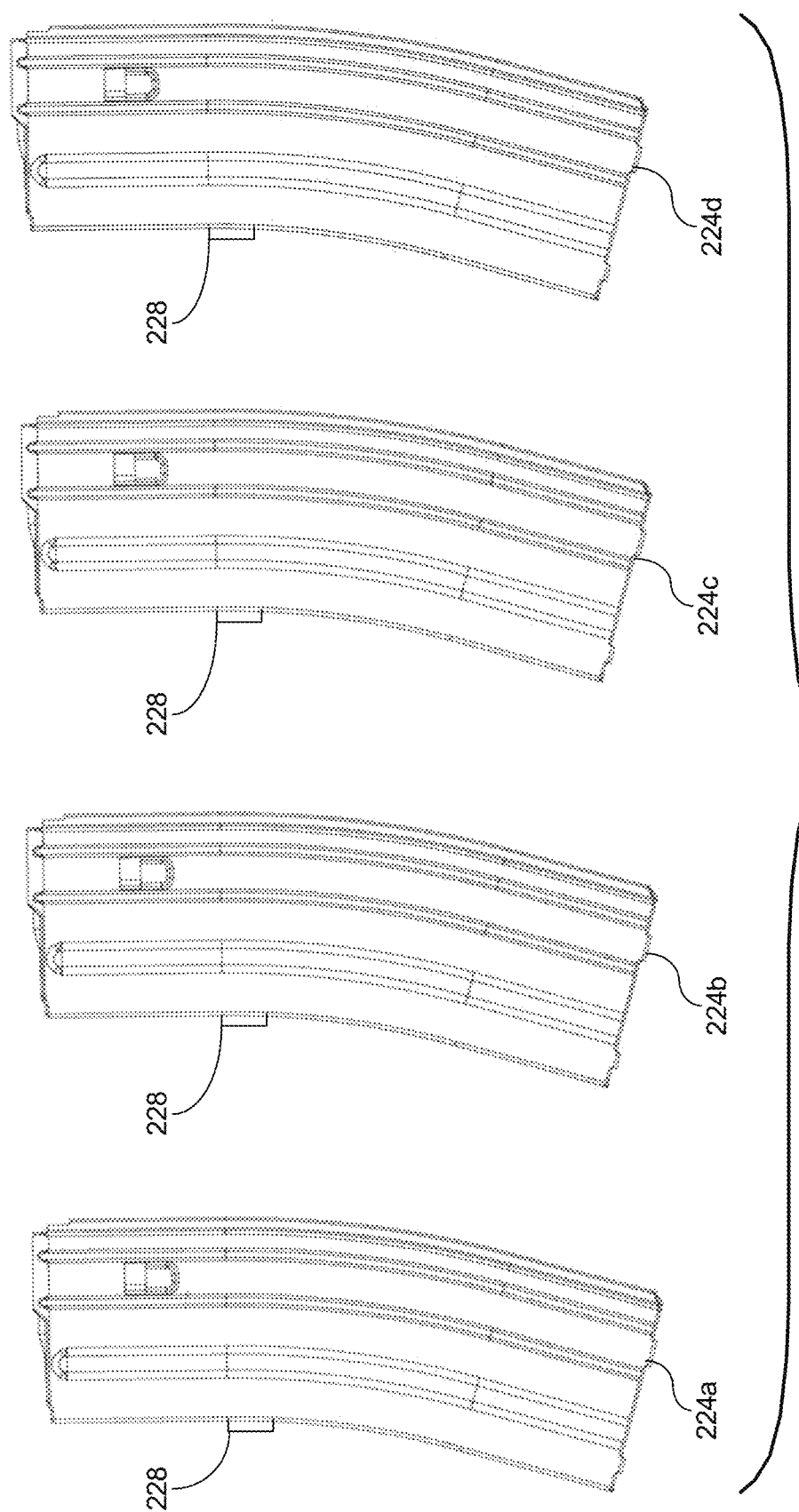
FIG. 8 illustrates a plurality of interchangeable ammunition magazines operable with the present weapon system.
Figure 9:
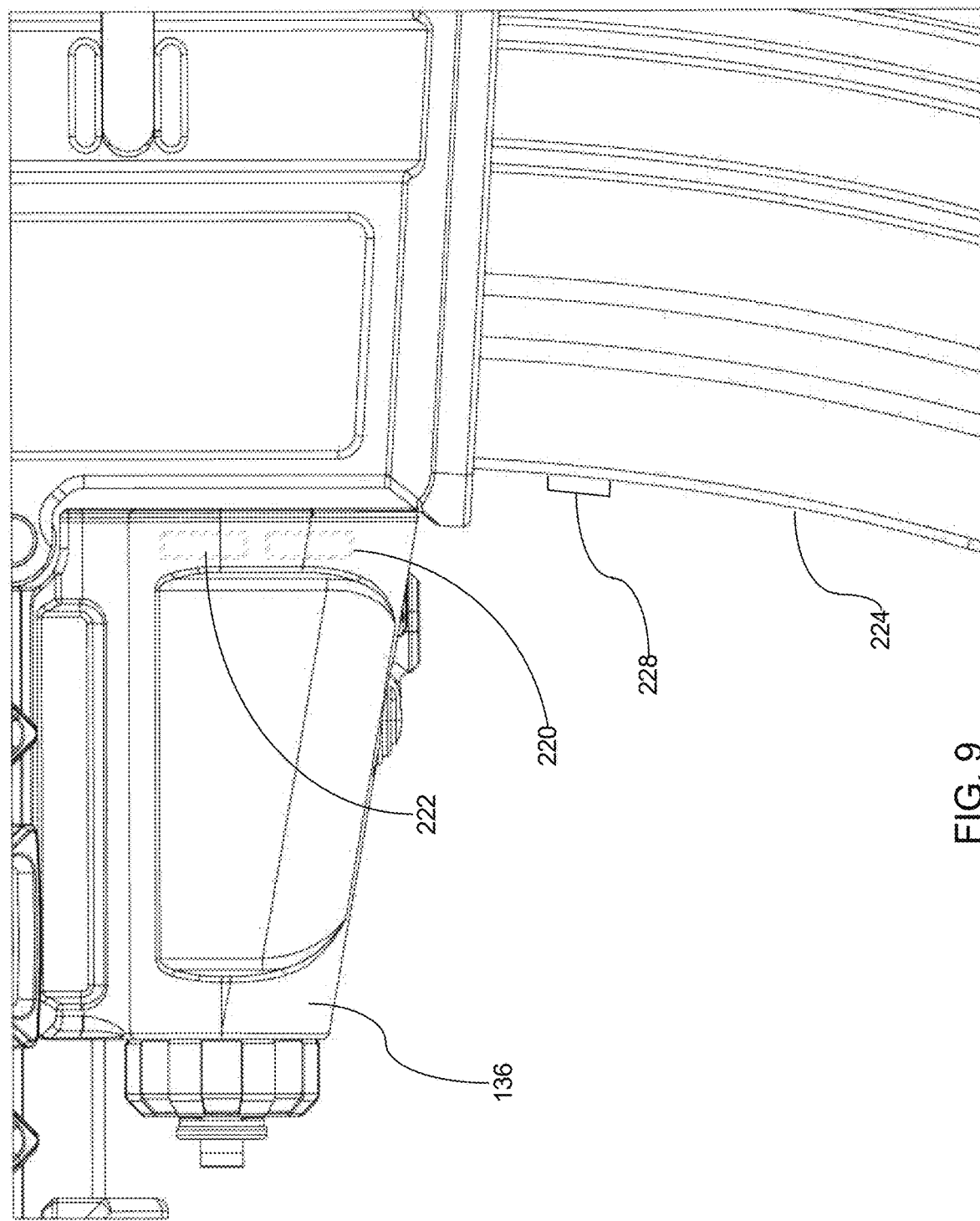
FIG. 9 is an enlarged, fragmentary side elevation view of the weapon system herein having a magazine with RFID tag inserted into the magazine well.
Figure 10:
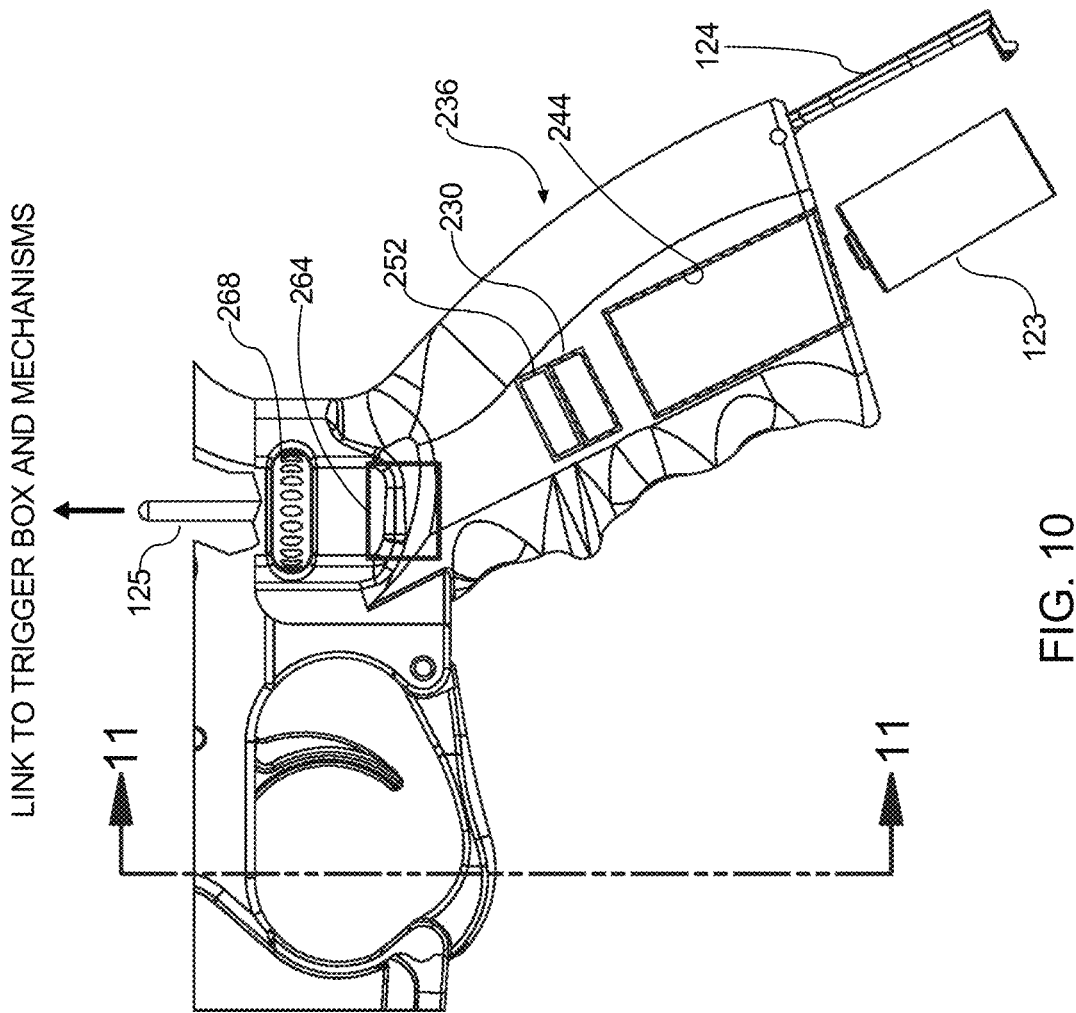
FIG. 10 is an enlarged, fragmentary side view illustrating components of the exemplary weapon system herein within the pistol grip and lower receiver.
Figure 11:
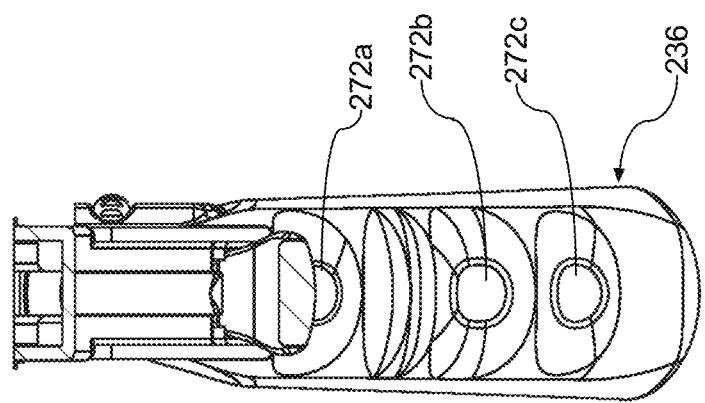
FIG. 11 is a cross-sectional view taken along line 11-11 appearing in FIG. 10.

In certain embodiments, as shown in FIG. 8, first one of the magazines 224a is a magazine for low velocity rounds such as low velocity (subsonic) 0.300 AAC Blackout rounds, and a second one of the magazines 224b is a magazine for high velocity (supersonic) 0.300 AAC Blackout rounds, a third one of the magazines 224c is a magazine for saboted rounds, e.g., Sabot Light Armor Penetrator (SLAP) rounds such as 0.300 ACC Blackout SLAP rounds, and a fourth one of the magazines 224d is a magazine for training rounds. It will be recognized that other ammunition types are also contemplated.

In certain embodiments, the ammunition type is logged in an ammunition database 312 stored in the memory 168 and may be displayed to the user on the display 176, e.g., as an item of information accessed by the user using scroll buttons 268 on the handguard assembly 108, as described below.

In operation, the RFID reader 220 reads the data representative of the round type contained on the RFID tag 228 of the installed magazine 224. The data is transmitted via the accessory platform 128 and the circuit 126 to the accessory device 140 and stored in the memory 168. In certain embodiments, environmental sensors 501 collect data regarding various environmental parameters, such as outside temperature, directional orientation, etc. The environmental data is transmitted to the processor 164 and may be stored in the memory 168. The processor 164 then calculates the sight trajectory based on ballistics information for the detected ammunition type as well as other factors, such as the distance to the target as determined using the range finder 196 as described above. In certain embodiments, the firing trajectory is adjusted based on the processor's calculations, via a stepper motor selectively advancing and retracting a bearing against the optical bench of an aligned sighting device.

In certain embodiments, when the installed magazine is a training round, the aiming mark from the reflex sight is configured to appear as a green dot. In certain embodiments, when the installed magazine is a non-training round, the aiming mark from the reflex sight is configured to appear as a green dot. It will be recognized that other reticle shapes, such as rings, cross hairs, and the like, are also contemplated.

In certain embodiments, the handgrip 236 further comprises a power source 123. One or more batteries 123 are received within an interior battery compartment 244 defined in the handgrip 236. In certain embodiments, the handgrip includes a battery cap 124. In certain embodiments, the handgrip 236 is coupled to an RF transceiver, such as the Bluetooth transceiver 222. Circuitry within the compartment 244, which may include circuit elements printed circuit elements on a flexible substrate, electrically couple the terminals of the battery(ies) to circuit within the accessory platform to provide battery power and control signals to attached devices, such as the laser sight 140 and/or camera 340. In certain embodiments, a Coulomb counter or like circuit 230 is provided to output battery state of charge information to the device 140 via the circuit 126.

In certain embodiments, the handgrip 236 includes an RFID reader 252 for sensing the proximity of a tactical glove 256 carrying an RFID chip tag 260. In certain embodiments, the handgrip 236 includes an RF transceiver, such as a Bluetooth transceiver 253, allowing the handgrip 236 to couple with and communicate with the battery box 136, for example, to activate the weapon system. In certain embodiments, the proximity of the tactical glove is required to activate the weapon system. Alternatively, in certain embodiments, the weapon system includes a solenoid switch 264 operable to selectively engage a trigger lock when the glove 256 is not in proximity to the RFID reader 252 and to disengage the trigger lock when the glove 256 is in proximity to the RFID reader 252. In certain embodiments, the solenoid switch engages the trigger lock via a pin or plunger 125, which is operably connected to the trigger mechanisms, such that when the pin is inserted into the trigger mechanism, the trigger cannot be activated.

In certain embodiments, a rotary encoder 268 on the handguard 108 is electrically coupled to the laser sight via the accessory platform 128 is manually rotatable to allow the user to scroll through pages, menus, or other items of viewable information on the display 176. In alternative embodiments, scroll buttons may be used in placed of the rotary wheel, to scroll through pages, menus, or other items of viewable information on the display.

In certain embodiments, one or more user-programmable switches 272, e.g., configured as user-depressible buttons, are provided on the handgrip 236. Signals from the switches 272 are transmitted to the processor 164 via the accessory platform 104 for controlling operation of, for example, the laser sight 140, flashlight module 188, push-to-talk radio, and/or other device attached to the accessory platform 104. Exemplary functions which can be executed on the laser sight 140 using the buttons 272 include any one or more of laser selection, laser actuation, display operation, and navigation of a hierarchal menu structure or other graphical user interface on the display 176. In certain embodiments, the switches 272 include a first switch 272a, second switch 272b, and third switch 272c, which are user-programmable to allow the user to customize the function of each button.

In certain embodiments, the handgrip housing has an outer material having a good grip adhesion, such as silicone, and may have a textured or contoured surface for enhancing grip. The outer material may be flexible and resilient and disposed over the depressible push button switches 272.

In certain embodiments, the handgrip 236 is coupled to an RF transceiver, such as the Bluetooth transceiver 222, to allow the user to control operation of an associated device having a paired RF transceiver, such as a cell phone, smart phone, hand held data terminal, wearable device, or the like via the RF interface using one or more controls on the handgrip, such as one or more buttons or keys 272, the scroll buttons 268, and so forth. In certain embodiments, one or more of the buttons 272 actuate a push-to-talk function of an associated two-way communication system, e.g., via the Bluetooth transceiver 222. In certain embodiments, communication the associated device includes software for use in identification verification of the user to activate the weapon system.

Firearm barrel sensors on the firearm barrel 172 send signals representative of barrel conditions to the processor 164 via the circuit 126. In certain embodiments, the sensors include one or more temperature sensors 276, such as one or more thermocouples, for providing output signals representative of the temperature of the barrel 172. In certain embodiments, the sensors include one or more strain gauges 280 for providing output signals representative of the degree of mechanical stress or deformation that the barrel is undergoing, e.g., responsive to a round of ammunition being fired by the firearm 100. In certain embodiments, the sensors include one or more piezo electric sensors 284 for providing output signals representative of the degree of mechanical stress or deformation that the barrel is undergoing, e.g., responsive to a round of ammunition being fired by the firearm 100.

Exemplary barrels having sensors thereon are disclosed in commonly owned U.S. provisional application No. 62/446,222 filed Jan. 13, 2017 and commonly owned U.S. provisional application No. 62/513,738 filed Jun. 1, 2017. Each of the aforementioned provisional applications is incorporated here by reference in its entirety.

In certain embodiments, bullet projectile velocity is calculated by the processor 164, e.g., using the sensors 280 and 284. In certain embodiments, bullet velocity information is logged in a bullet velocity database 304 stored in the memory 168 and may be displayed to the user on the display 176, e.g., as an item of information accessed by the user using the scroll buttons 268.

In certain embodiments, barrel temperature is calculated by the processor 164, e.g., using the sensor 276. In certain embodiments, barrel temperature information is logged in a barrel temperature database 308 stored in the memory 168 and may be displayed to the user on the display 176, e.g., as an item of information accessed by the user using the scroll buttons 268.

In certain embodiments, signals from the strain gauges 280 and/or piezo electric sensors 284 are sent to the processor for signal processing and/or data storage. It will be recognized that the processor 164 may include and is intended to encompass associated signal processors such as analog-to-digital converters, digital signal processors, and the like, which may be implemented as functional modules within a single, e.g., general purpose, processing unit or as discrete or dedicated hardware processors.

In certain embodiments, the system continuously monitors the barrel sensors 276, 280, 284. Signal parameters indicative of a round being fired are detected and logged in a round count database 300 stored in the memory 168. The number of rounds fired may be displayed to the user on the display 176, e.g., as an item of information accessed by the user using the scroll buttons 268.

The firing of a round is a wear-creating event. In certain embodiments, each round that is fired is associated with an incremental unit of barrel wear. Each incremental unit of barrel wear is logged in a barrel wear database 316 stored in the memory 168. The accumulated wear is compared to a preselected wear limit, which may be, for example, the barrel wear (or estimated or predicted barrel wear) that is associated with a certain degree of accuracy loss. The accumulated barrel wear may be displayed in the display 176 and may be indicated in a number of ways, for example, as a percentage of barrel life remaining, calculated as:

$$100 \times (1 - \text{accumulated wear/wear limit})$$

or, alternatively, as a percentage of barrel life consumed:

$$100 \times \text{accumulated wear/wear limit}$$

A basic embodiment of the system may base the wear accumulation based solely on the number of rounds fired. In alternative embodiments, the severity of the wear created can be estimated based on other system parameters, such as the barrel temperature, which may be monitored and logged at periodic intervals in the barrel temperature database 308, or ammunition type, which may be read by the RFID reader 220 and logged in an ammunition database 362 in the memory 168.

For example, rounds fired when the barrel is at a high temperature generate increments of barrel wear that are more severe than rounds fired when the barrel is not at a high temperature. Similarly, rounds that have increased quantities primer and propellant/powder (e.g., high velocity rounds) generate increments of barrel wear that are more severe than rounds that have lower amounts of primer and propellant/powder (e.g., low velocity rounds). The severity of barrel wear is affected by the type of primer and propellant/powder in the round.

In certain embodiments, the system estimates the incremental wear associated with firing each round and quantifies the severities based on round type, barrel temperature, rate of fire, and so forth, which provides an improved estimate of barrel wear over wear estimates based solely on the number of rounds fired. In certain embodiments, the severity of wear can be further estimated based on predicted interactions of firearm parameters with each other and/or with interactions of firearm parameters and the current accumulated barrel wear. In certain embodiments, the estimated severity of a given firing event is used to denominate the incremental wear associated with each firing event into units of normalized rounds fired and, as rounds are fired, wear increments in normalized units are added to the preexisting cumulative barrel wear stored in the wear database 316.

Referring now to FIGS. 21-34, there is illustrated a further embodiment system comprising an laser sight accessory device 140 attached to the accessory rail 128, the accessory device further having an integrated camera 400, such as a pin hole camera. The camera 400 is rear facing and is configured to image a field of view 401 which encompasses at least the user's eye region and, in certain embodiments, the user's facial region. The accessory device may be a BOSS™ system available from Wilcox Industries Corp. of Newington, N.H.

The rear facing camera 400 is located on the top of the unit 140 and camera serves multiple purposes, including: (1) reading a bar code or other optically readable indicia on associated eyewear 412 worn by the user for identification of the operator; (2) performing facial recognition of the operator for user verification/authentication purposes; (3) tracking the positioning of the operator's eye or eyes relative to the weapon to verify what the operator is viewing during operation of the weapon, and (4) allowing the operator to control operation of the unit 140 to perform a ranging function and menu activation and selection via optical interaction with the system.

The eyewear 412 feature a bar code or other optically readable indicia 402 and an integrated near-eye display screen 403. In certain embodiments, the near-eye display 403 is see-through to permit the user to view the surrounding environment therethrough. In certain embodiments, the display 403 is configured to selectably display one or more of: a system menu, sighting system 140 menu options, sighting system 140 statistical information such as range, battery power level, user confirmation status, and user biometric data as selected by the user via the optical interface using the camera 400 or the smart glove 256 interface.

The present development allows the system to conform to a single user via dual factor user verification/authentication and allows the operator to control the system without the need for additional devices which slow response time.

The eyewear 400 may be spectacles, goggles, glasses, safety glasses, and so forth. In certain embodiments, the eyewear 412 includes vision corrective lenses. In certain embodiments, the eyewear 412 is configured to protect the user's eyes and the surrounding region from particulates, water, chemicals, and so forth from striking or entering the user's eyes. In certain embodiments, the eyewear 412 includes a lens for filtering one or more wavelengths of electromagnetic radiation. In certain embodiments, the eyewear 412 is configured as sunglasses. In certain embodiments, the eyewear 412 includes polarized lenses.

The eyewear includes a machine-readable indicia 402, such as a one-dimensional bar code, two-dimensional bar code, QR code, or other optically readable indicia. The bar code or other indicia may appear on a label adhered to the eyewear 412, or may be embedded, engraved, etched, sandwiched between lens layers, etc., in the eyewear 412. In certain embodiments, the barcode or other indicia 402 is advantageously positioned at or near the bridge portion of the eyewear, but it will be recognized that the barcode or other indicia may be placed at any other location suitable on the eyewear 412 for imaging by the camera 400, including without limitation the lens portion of the frame portion of the eyewear.

In operation, the camera 400 reads the indicia 402 of the eyewear 412, which encodes information that serves to identify the user and can be used to retrieve the prior history of use of the system of the user (or of multiple users). In certain embodiments, the user history/data is output to the eyewear display 403. In certain embodiments, the user history/data is output to the display 176. In certain embodiments, the user history/data is output to an external device such as portable computing device 510 or smartphone 520 (see FIG. 24), or other storage medium. In certain embodiments, the identified user's data settings (e.g., data settings 325 stored in the memory 168) are used to configure the device 140 and, optionally, other attached components of the weapon system, with the user's preferences or stored settings. In certain embodiments, the eyewear 412 with barcode 402 serves as a possession-type of discriminator or authentication factor to unlock or otherwise permit the user to operate the weapon system.

In certain embodiments, biometric data may be used, either in addition to or as an alternative to, the barcode/indicia 402 for the purpose of identifying the user, retrieving user data and history, configuring the weapon system, and/or permitting access to or unlocking the weapon system. In embodiments employing biometric data, such data may be facial recognition data or ocular data, such as iris recognition data, eye vein verification data, or retinal scan data. In this manner, the facial recognition data and/or ocular or retinal scan data serve as an inherence type discriminator or authentication factor to unlock or otherwise permit the user to operate the weapon system. In certain embodiments, the user's facial features, retina, and/or ocular features are imaged by the camera 400.

In alternative embodiments, a camera-equipped smart phone 520 or other mobile or hand-held computing device 510 may be used to image one or more of the bar code/indicia 402, user's retina, or user's facial features for identification of the user. Imaged data from the device 510 or 520 may be transmitted to the accessory device 140 for processing by the processor 164 or, alternatively, for processing by a processor of the smartphone 520 or portable computing device 510. In certain embodiments, data is transmitted between the powered rail system and the devices 500, 510, 520 via the remote power supply/battery box 236 as described above.

In certain embodiments, the eyewear 412 is employed in lieu of the glove 256 equipped with RFID 260 described above. In other embodiments, the eyewear 412 is employed in combination the glove 256 equipped with RFID 260 described above.

Figure 22:
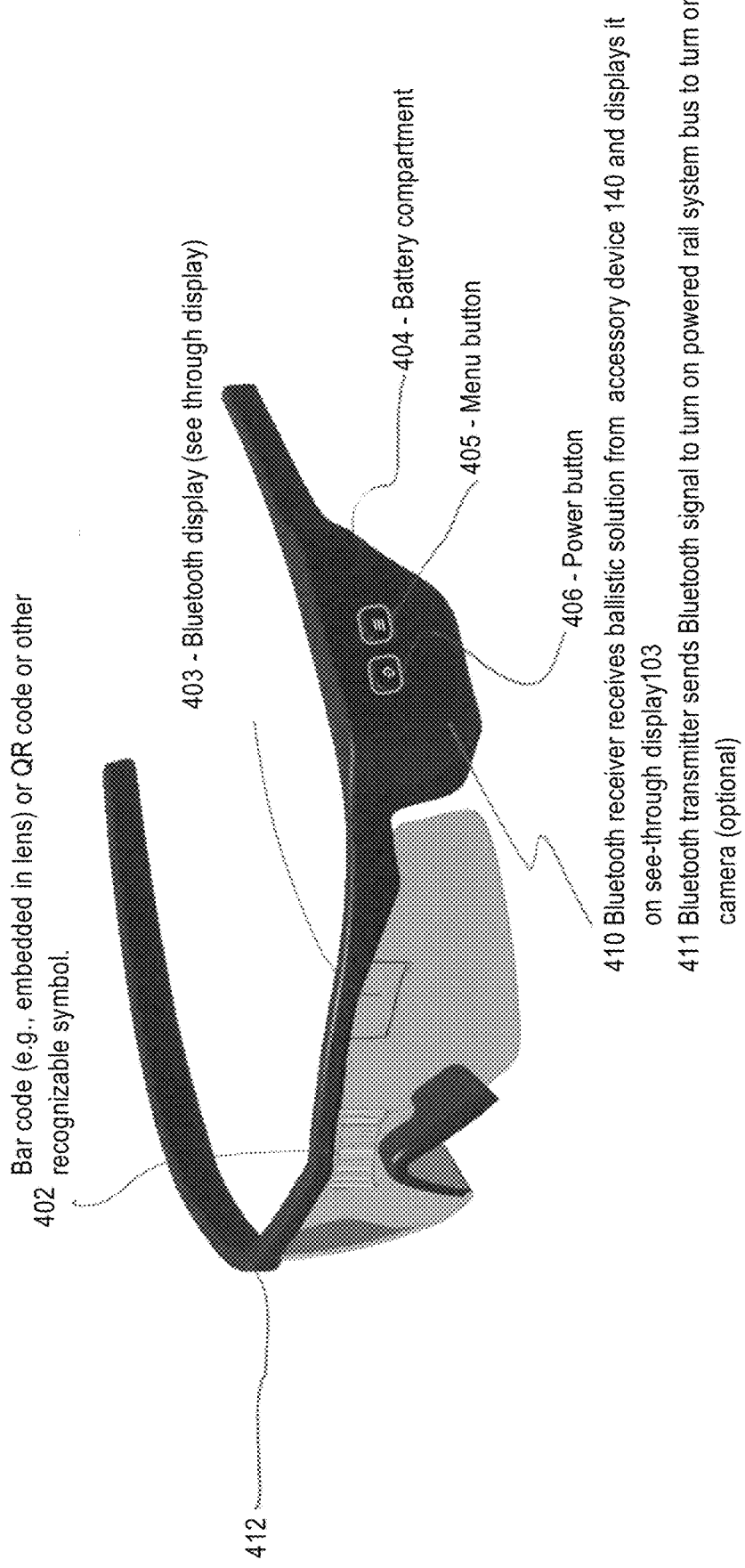
FIG. 22 is an isometric view of the accessory eyewear device appearing in FIG. 21.
Figures 23A, 23B:
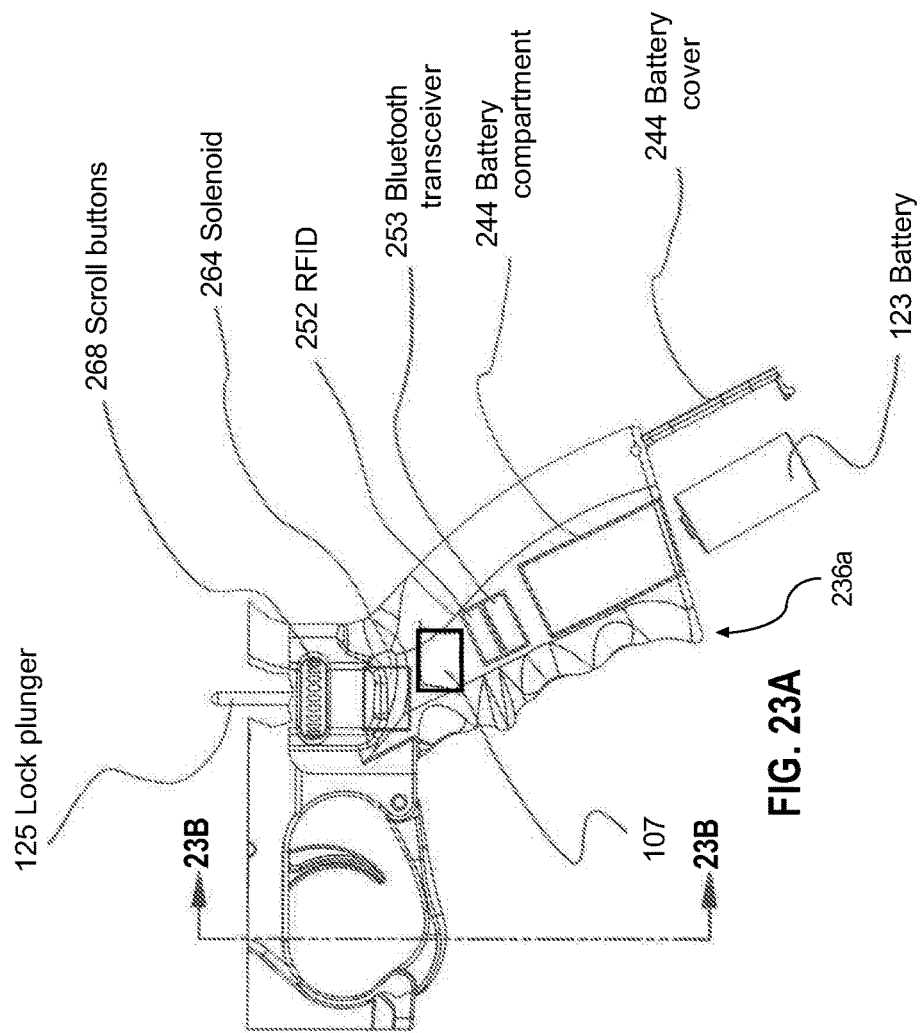
FIG. 23A is an enlarged, fragmentary side view illustrating components of the exemplary weapon system herein within the pistol grip and lower receiver.
FIG. 23B is a cross-sectional view taken along line 23-B-23B appearing in FIG. 23A.
Figure 25:
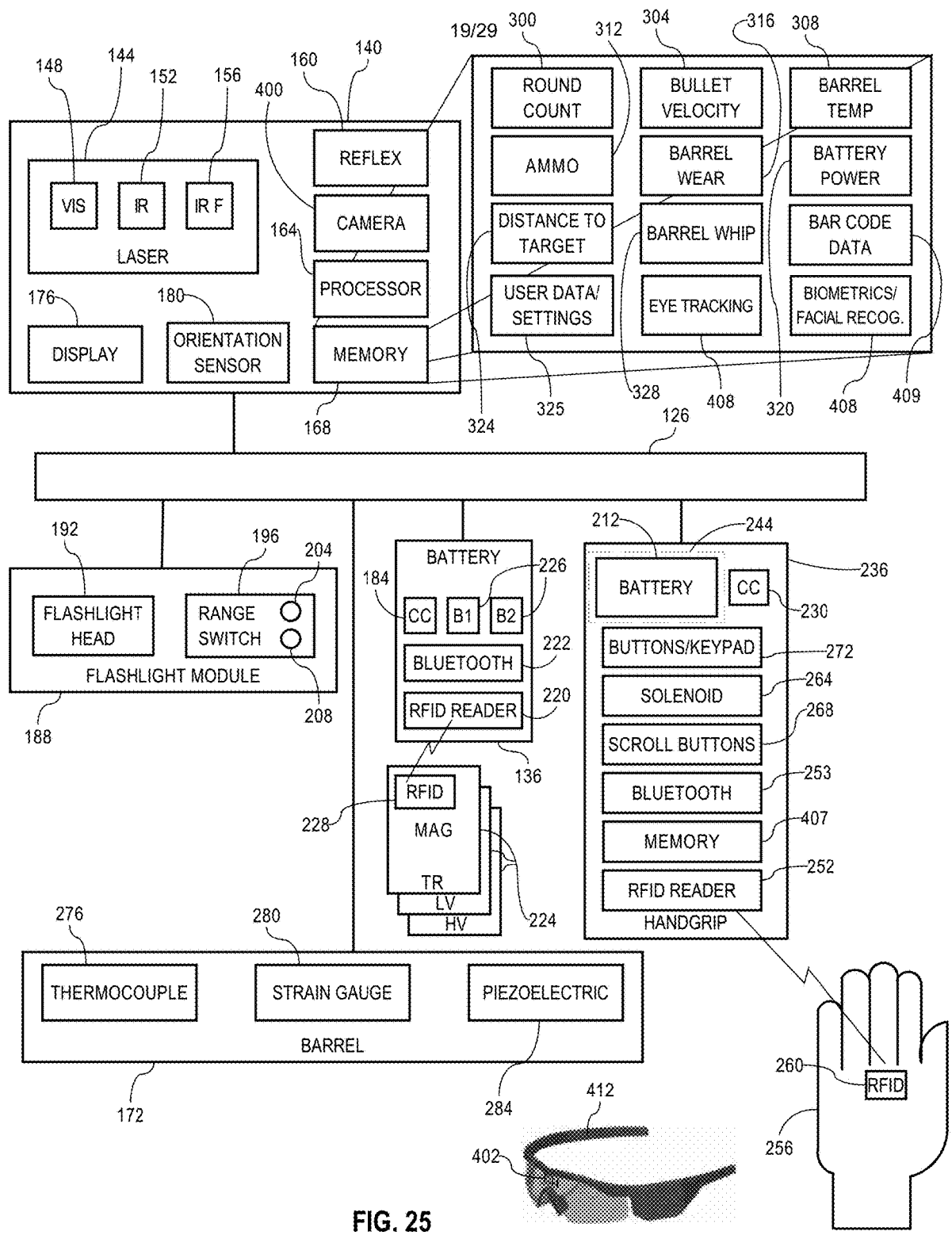
FIG. 25 is a block diagram illustrating an exemplary weapon system including an accessory eyewear device and a tactical glove.
Figure 26:
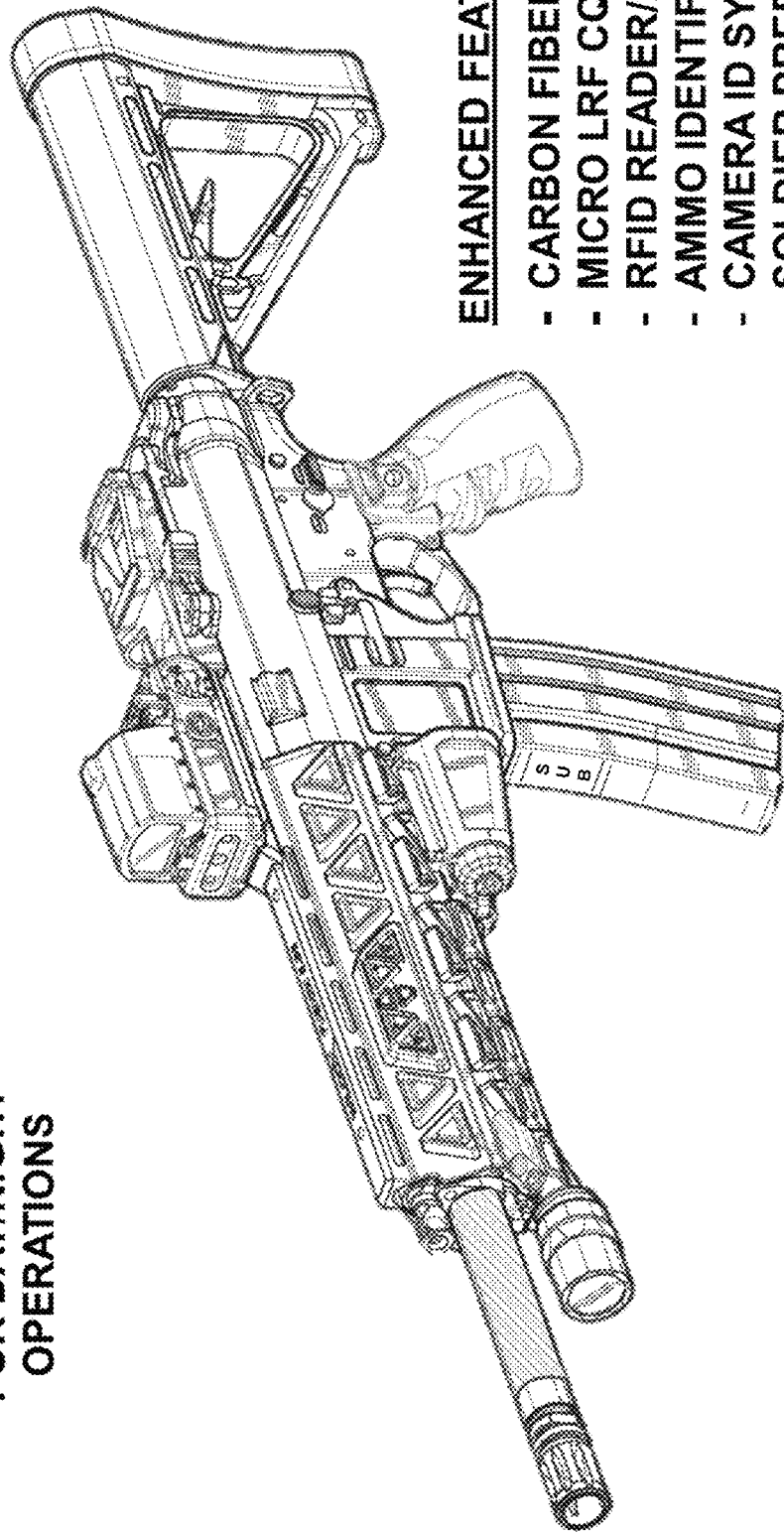
FIG. 26 is an isometric view of the weapon system appearing in FIG. 1, with the second accessory device removed.
Figure 27:
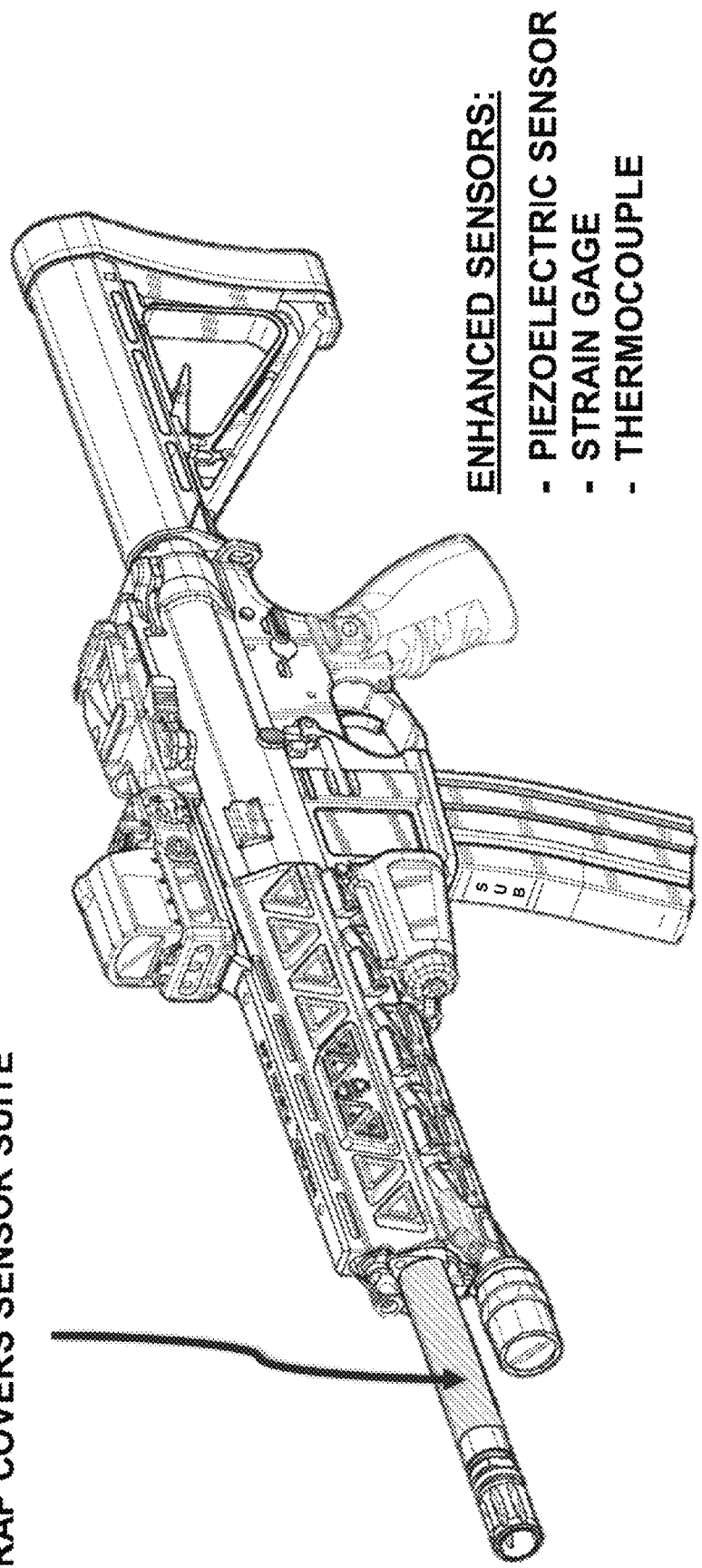
FIG. 27 is an isometric view of the weapon system appearing in FIG. 26.
Figure 28:
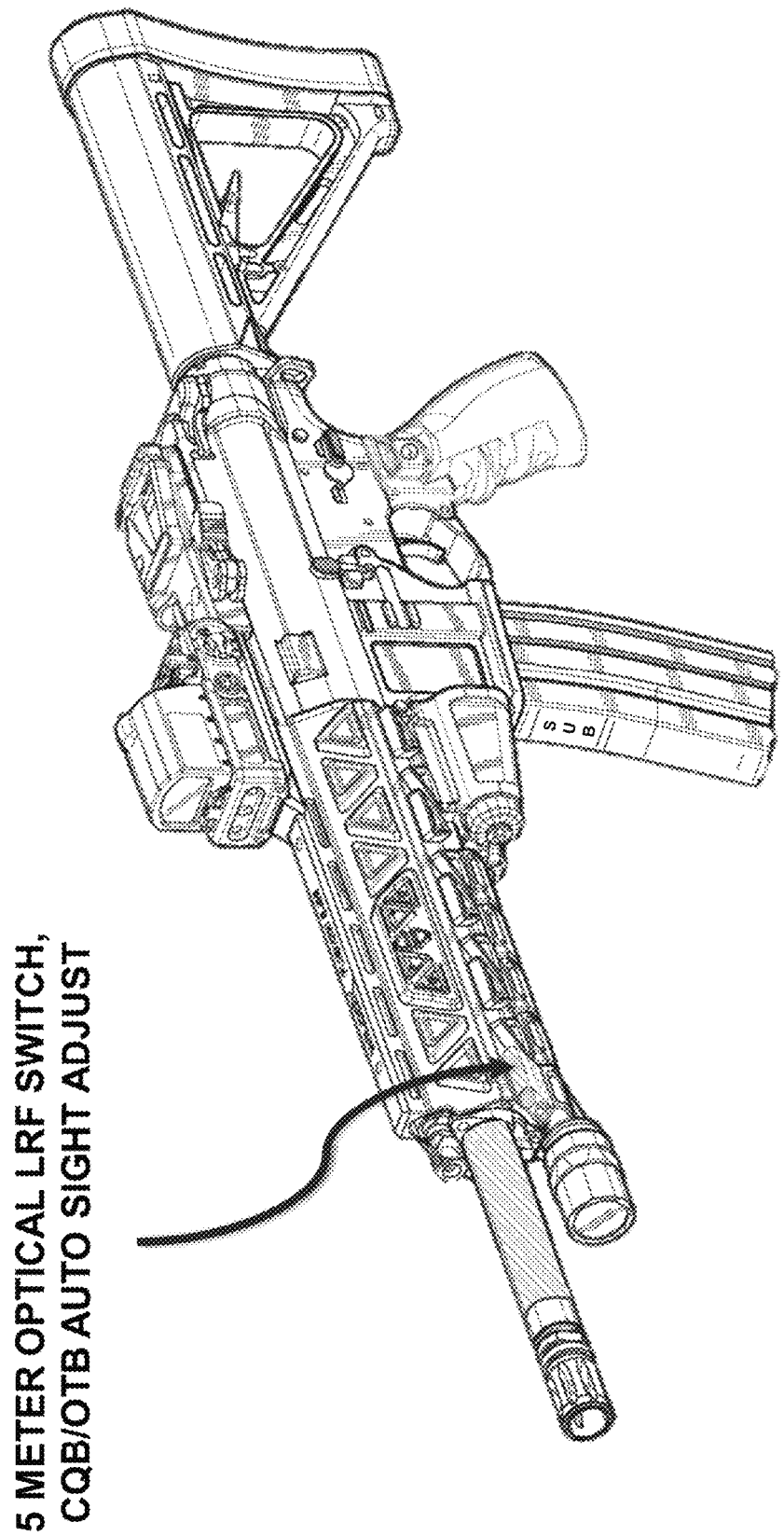
FIG. 28 is an isometric view of the weapon system appearing in FIG. 26.
Figure 29:
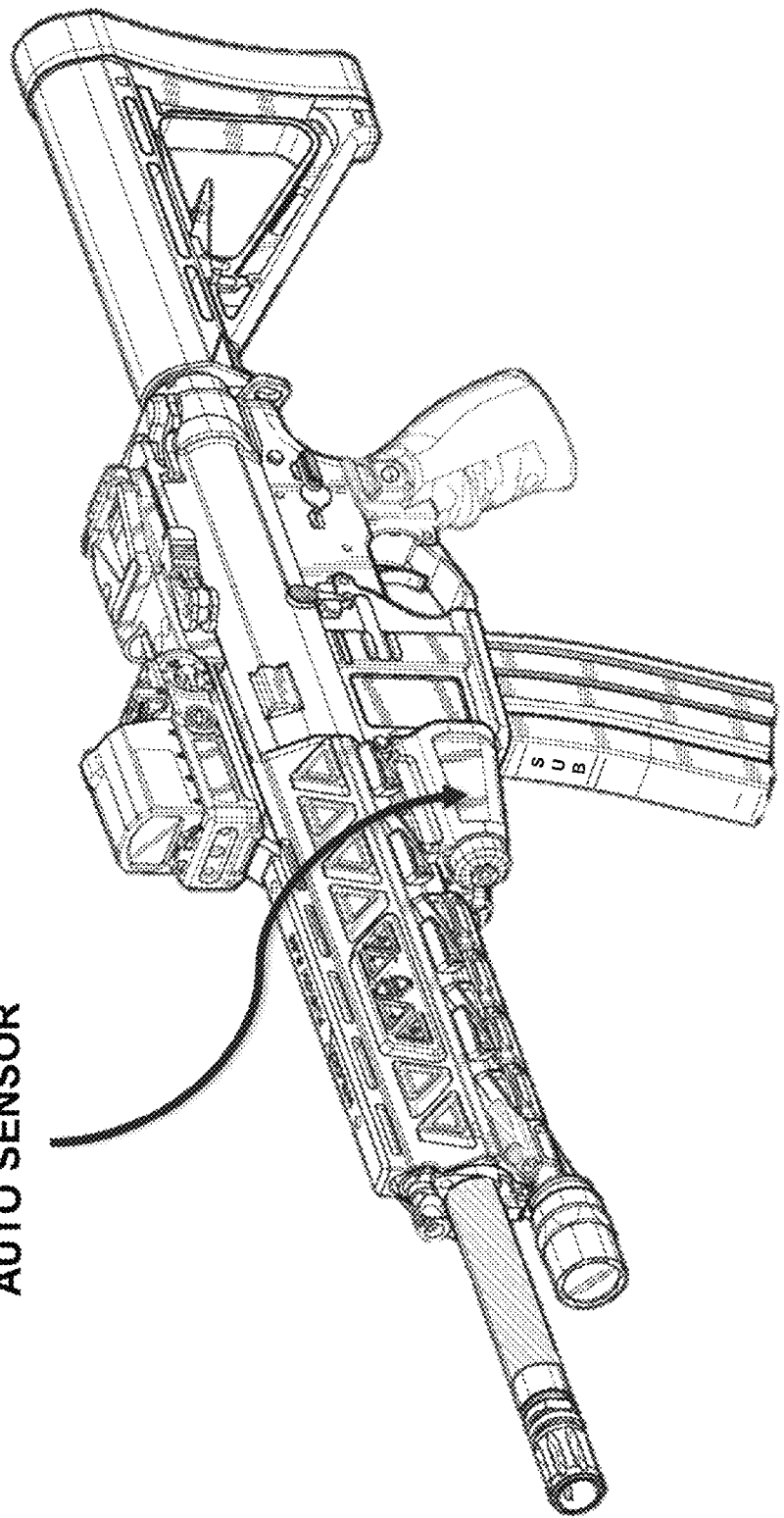
FIG. 29 is an isometric view of the weapon system appearing in FIG. 26.
Figure 30:
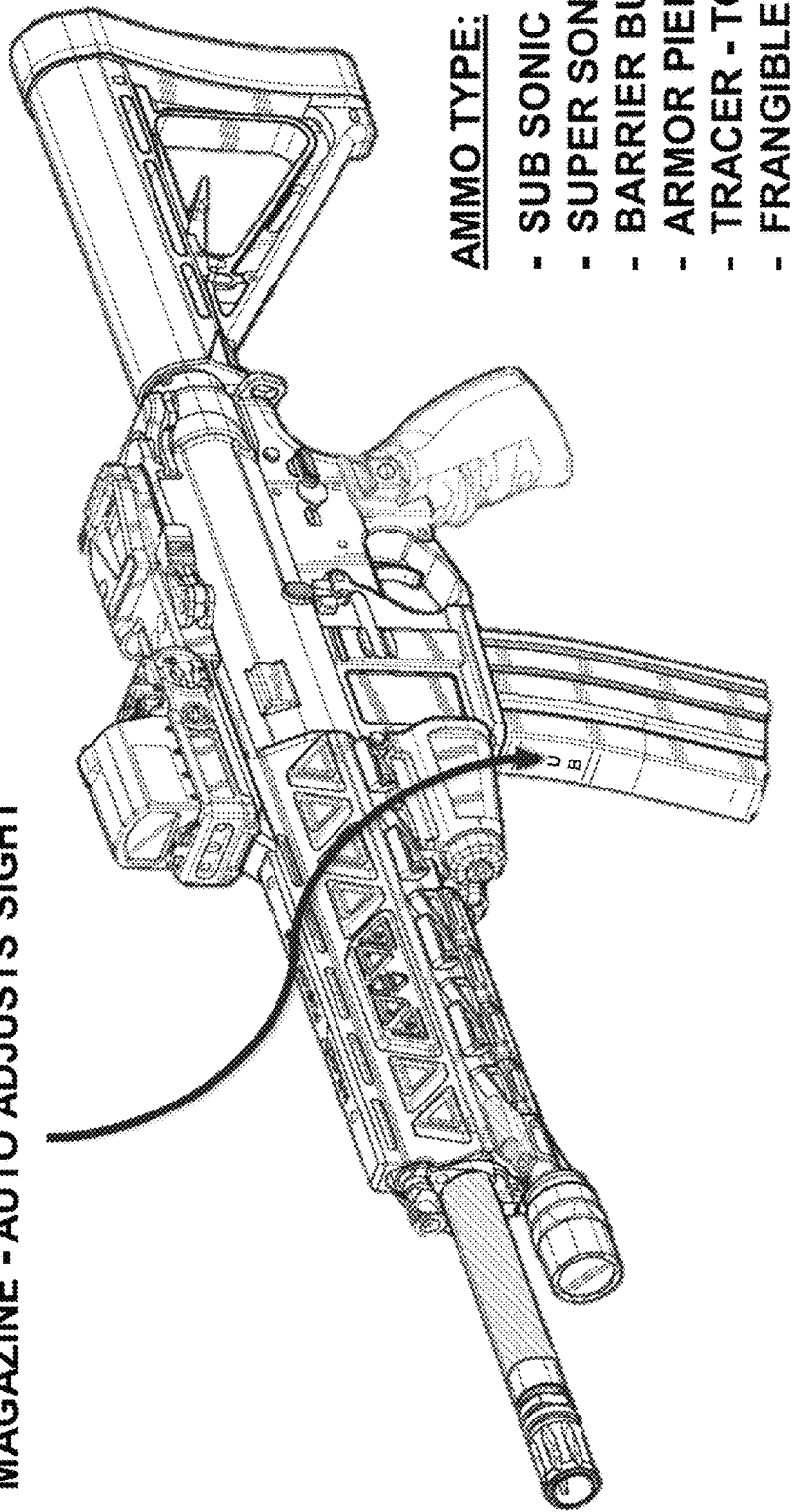
FIG. 30 is an isometric view of the weapon system appearing in FIG. 26.
Figure 31:
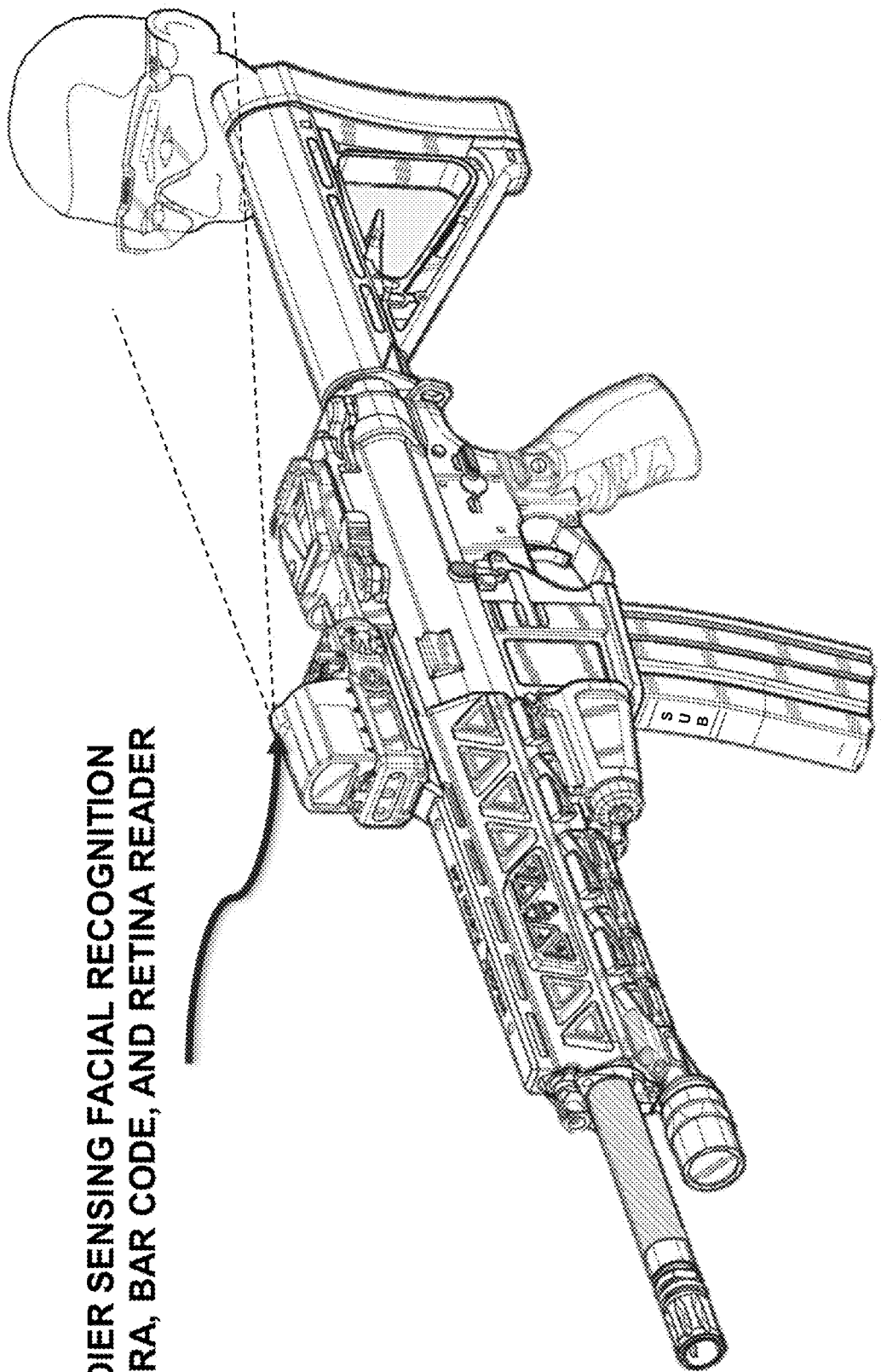
FIG. 31 is an isometric view of the weapon system appearing in FIG. 26 including an accessory eyewear device.
Figure 32:
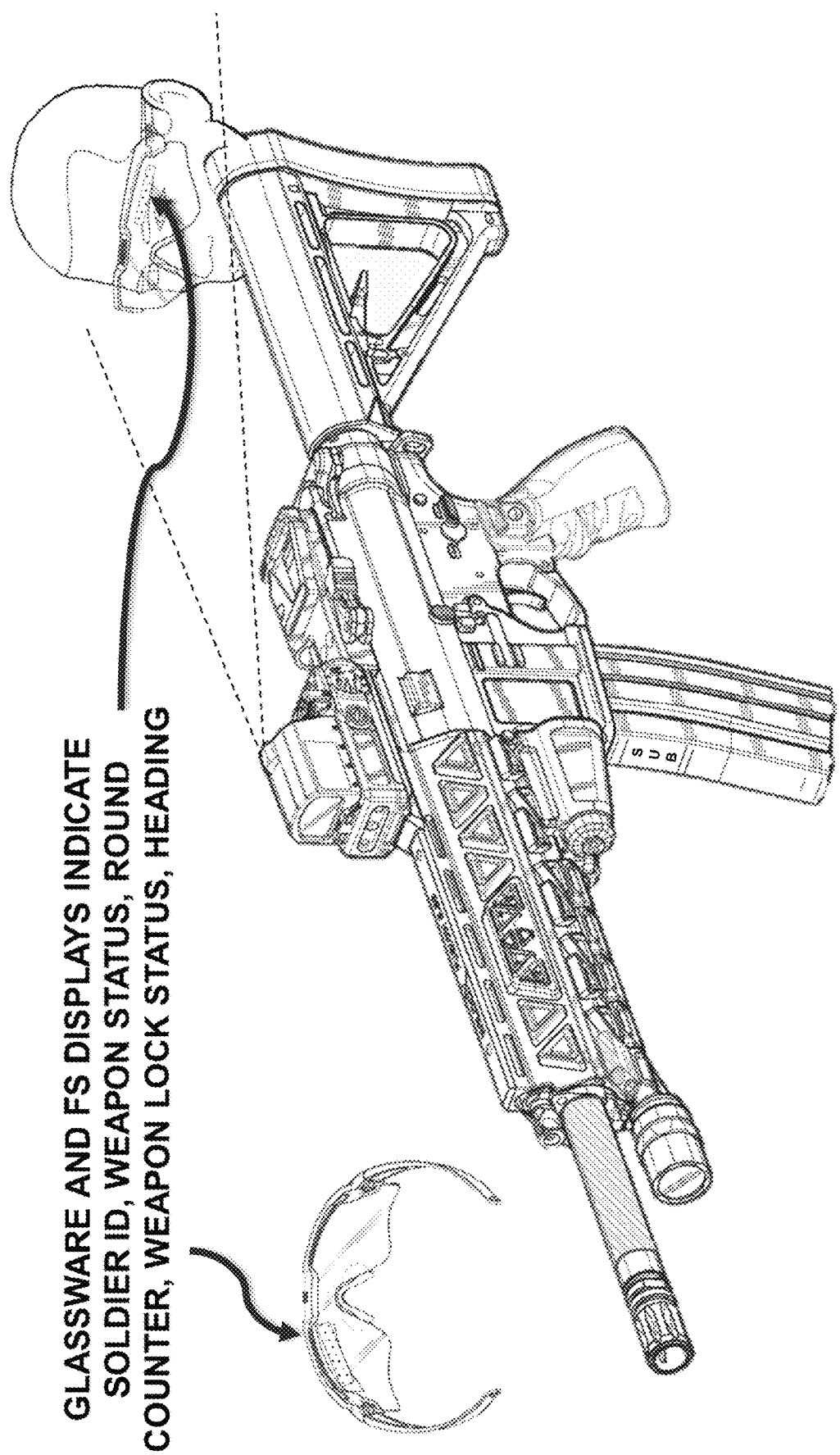
FIG. 32 is an isometric view of the weapon system and accessory eyewear device appearing in FIG. 31.
Figure 33:
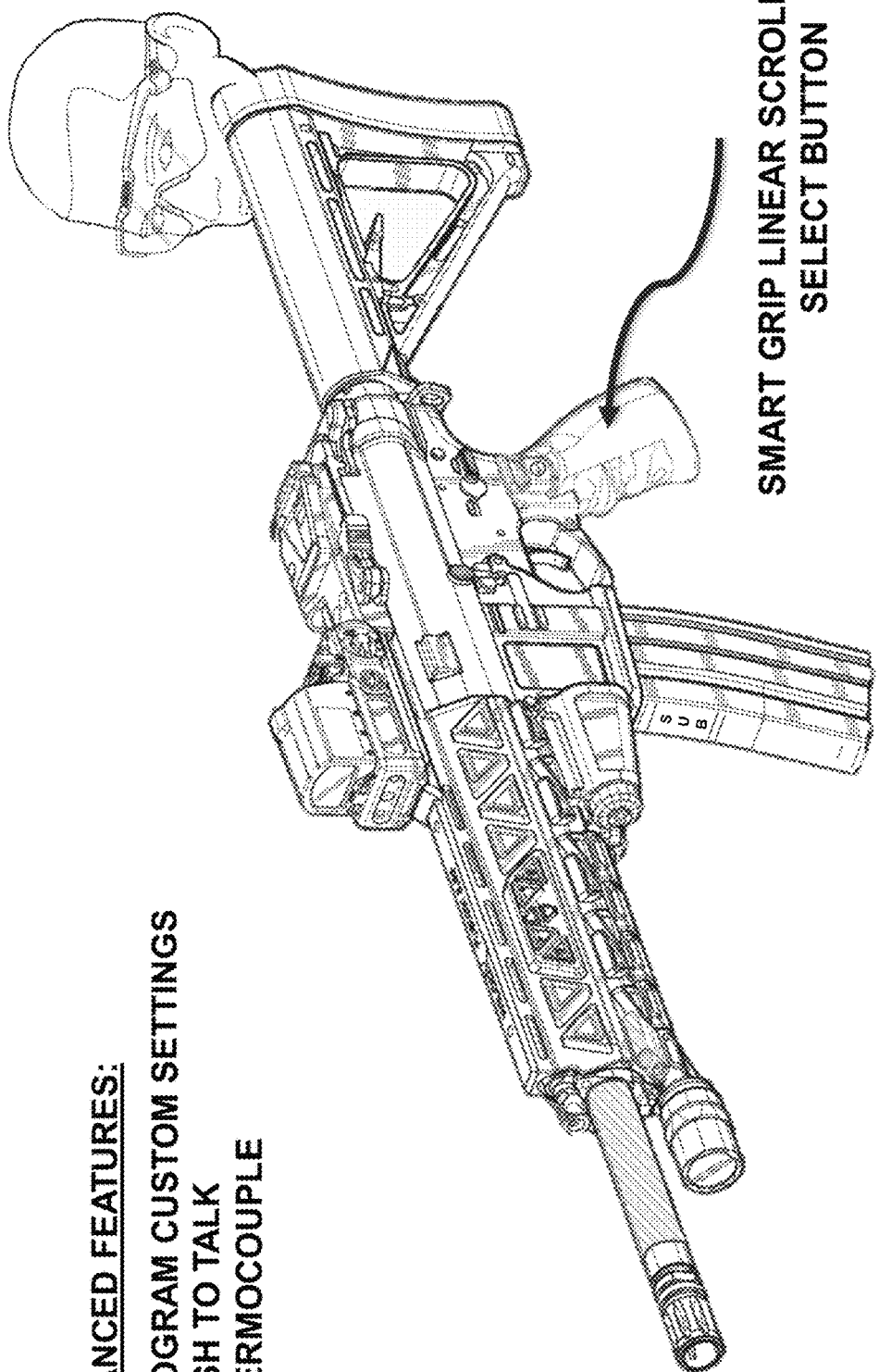
FIG. 33 is an isometric view of the weapon system and accessory eyewear device appearing in FIG. 31.
Figure 34:
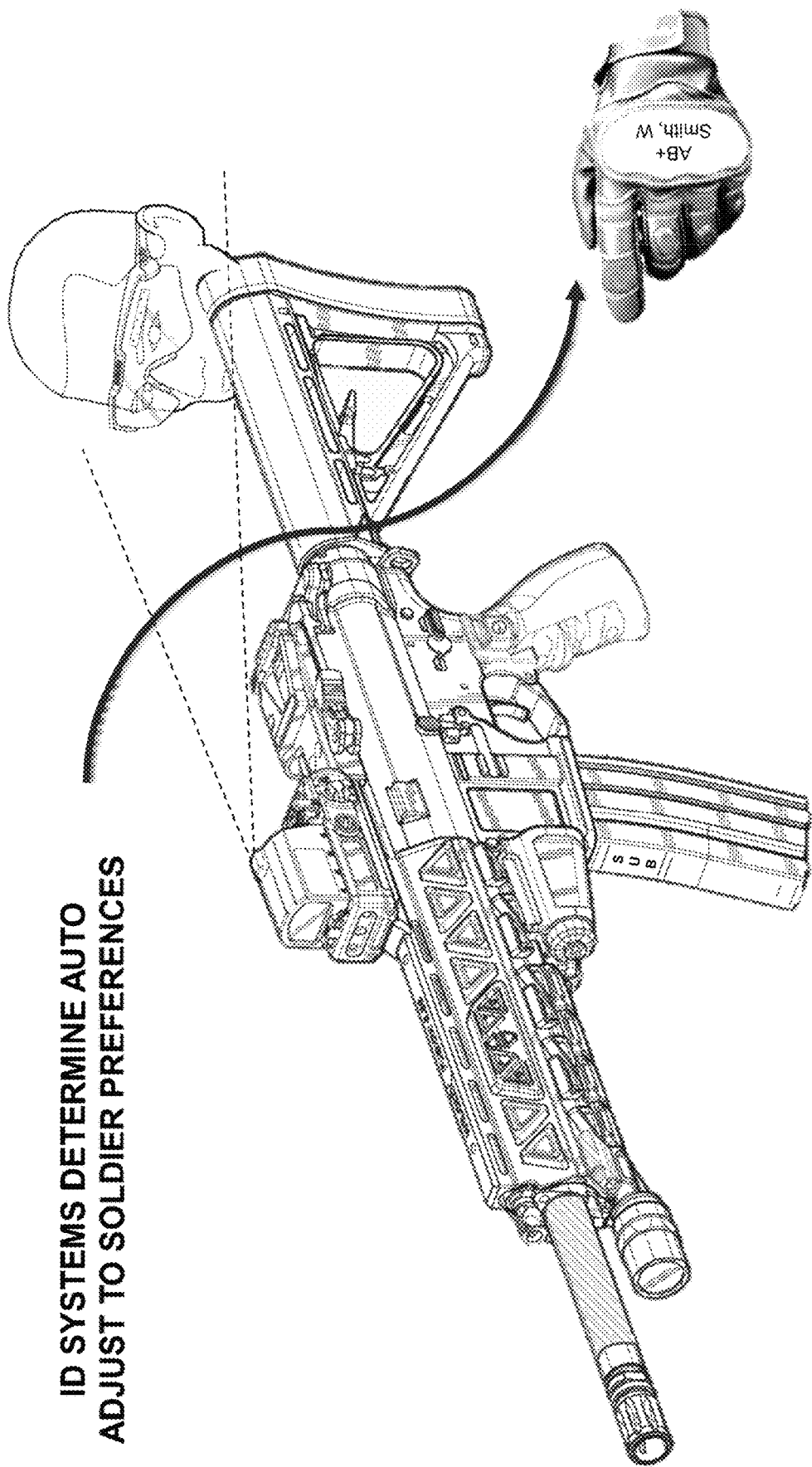
FIG. 34 is an isometric view of the weapon system including an accessory eyewear device and tactical glove appearing in FIG. 25.

FIG. 22 is an enlarged view of the eyewear 412 illustrating the barcode/indicia 402 on/in the lens portion thereof. In certain embodiments, the eyewear 412 includes a transparent or translucent display 403 which is viewable within the user's field of view when wearing the eyewear 412. A housing on one of the eyewear temple pieces encloses the associated display driver electronics for driving the display 403 as well as an RF (e.g., Bluetooth) receiver and transceiver pair 410, 411. A battery compartment 404 is also contained within the temple piece housing for receiving a battery power supply for powering the display and the Bluetooth receiver and transceiver. One or more keys or buttons are also provided on the housing for controlling operation of the display system. In certain embodiments, the buttons/keys include a power button 406 for powering the eyewear 412 on and a menu button 405 for navigating an onscreen menu interface or other on-screen graphical user interface. In certain embodiments, the camera 400 tracks the user's eye movements, to determine what the operator is viewing during operation. In certain embodiments, the camera 400 provides an alternative input means using eye tracking information to control operation of the powered rail system and/or the sighting system 140, e.g., by navigating a menu-based on-screen user interface, without the need to use input keys or buttons, scroll wheels, etc.

In operation, the Bluetooth receiver 410 receives ballistic solution from the accessory device 140 and displays it on the display 403. In certain embodiments, the Bluetooth transmitter 411 and receiver 410 are paired with the Bluetooth transceiver 253 in the handgrip 236 and the ballistic solution information is received by the Bluetooth transceiver module 253 via the powered rail system bus 126, which, in turn, transmits the ballistic solution to the Bluetooth receiver 410 for output to the see-through display 403.

In certain, optional, embodiments, the Bluetooth transmitter 411 sends a signal to the device 140 via the Bluetooth module 253 to turn on the powered rail system bus 126 and, in turn, turn on the camera 400 to identify the user, e.g., by scanning the barcode/indicia 402, scanning the user's facial features, and/or scanning the user's retina. In alternative embodiments, the user is verified using the fob 500, smartphone 520, or other computing device 510. In certain embodiments, one or more of the units 500, 510, 520 can be used to identify the user and thereby serve as a possession-type of authentication factor. After the user's identified is determined, the accessory device 140 and/or eyewear 412 can be programmed using stored user data and user history in the memory 107, memory 168, and/or a memory of the unit 510 or 520. In certain embodiments, one of the units 510, 520 can be used to program the accessory device 140 and/or eyewear 412 via an application program and user interface on the device 510, 520.

In certain embodiments, wireless communications between devices such as between the fob 500 and the remote power supply 136 as well as Bluetooth communications between the power supply 136, grip 236, and eyewear 412 is encrypted. In certain embodiments, wireless communications may use rolling code security as is known in connection with garage door openers or other keyless entry systems, although other methods of encrypting RF transmissions are also contemplated. In certain embodiments, the PDA 510 or smartphone 520 is used to scan the eyewear 412 and program the memory 407 in the powered rail system and/or the memory 168 in the accessory device 140. In certain embodiments, the units 510 or 520 are used to process facial recognition and program the memory 168 in the accessory device 140 and/or the memory 407 in the grip 236.

Figure 35:
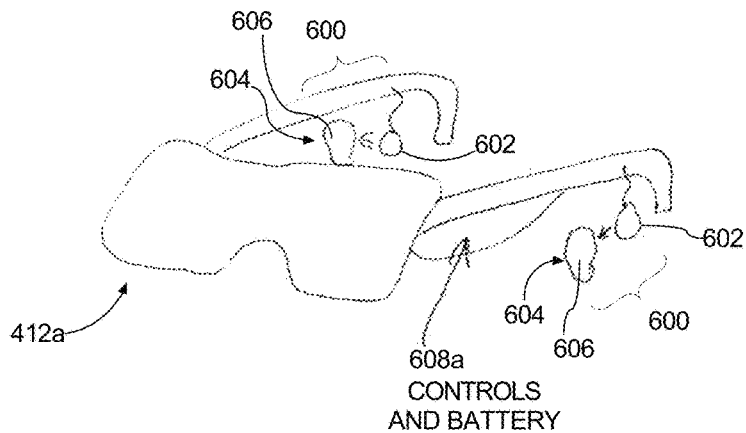
FIG. 35 is an isometric view of an accessory eyewear device having a pair of ear-fitting units.
Figure 36:
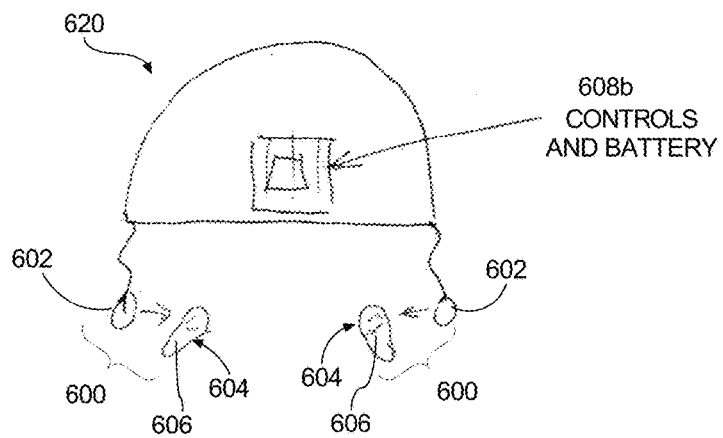
FIG. 36 is a rear view of a helmet having the ear-fitting units of FIG. 35.
Figure 37:
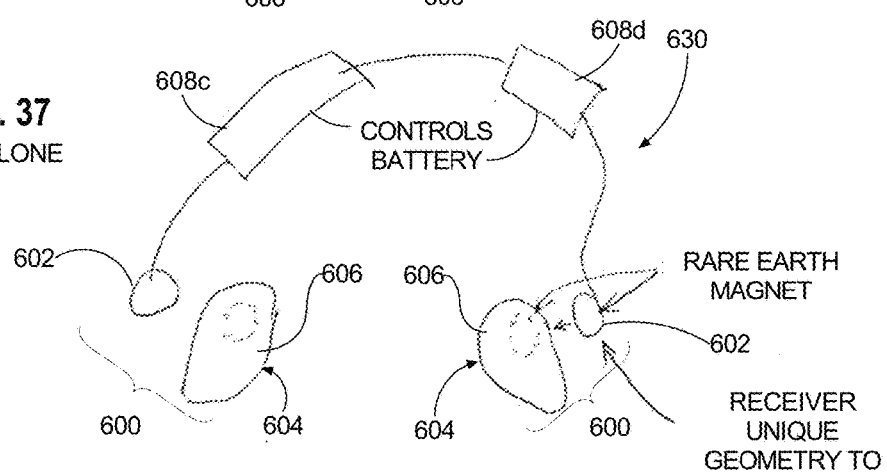
FIG. 37 is a front view of a headset having the ear-fitting units of FIG. 35.

In a further aspect, with reference now to FIGS. 35-37, the present development relates to an in-ear communications apparatus which provides a communications function and is customized to also provide a discrimination function to prevent an enemy or unauthorized person from using the apparatus. Although the illustrated embodiments depict two-ear systems, it will be recognized that systems for use in a single ear are also contemplated, e.g., wherein one of the earpieces is omitted or is replaced with a passive hearing protection device.

The in-ear communications apparatus herein include left and right earpieces 600, each earpiece 600 including an electrical connector 602 removably attached to an ear-fitting unit 604. The connector 602 and ear-fitting unit 604 preferably have a have a keyed geometry to allow the devices to connect in one way. In certain embodiments, small but powerful magnets (e.g., rare earth magnets), are employed to secure the electrical connector 602 to the ear-fitting unit 604. In certain embodiment, each earpiece 600 has a pair of aligned opposing magnets. In other embodiments, either one of the connector 602 or the ear-fitting unit 604 has a magnet and the other has a piece of magnetically attractive material.

The connectors 602 are coupled to a control unit 608 via cables 610 which provide power, data, and signal transfer between the earpieces 600 and the battery and processing electronics within the control unit 608. The connector 602 will automatically connect to the ear-fitting unit 604 due to the geometrically keyed configuration and the magnetic attraction between the two components. In the event the connector 602 and ear-fitting unit 604 become temporarily separated, e.g., when pulled apart due to being snagged, they will tend to immediately reconnect due to the magnetic attraction between the magnetic fastener elements on the connector 602 and ear-fitting unit 604. In certain embodiments, the cable components 610 have a length and/or shape that cause them to remain within the range of magnetic attraction between the magnetic fastener elements when the ear fitting units 604 are in the ears of the user and the spectacles 412a, helmet 620 or headset 630 are donned by the user.

The ear fitting units 604 may have an internal power supply, an external power supply, or preferably both. Because of the limited size of the earplug 604, it is limited as to the size of the power supply it can accommodate internally. The external control module 608 can accommodate a much larger battery to allow the earplug units to operate for long period of time.

Each ear-fitting unit 604 includes an exterior enclosure 606 which is custom fitted to the precise shape of a particular user's ear to be worn in the pinna/ear canal region of the user's ear. The enclosure 606 houses an audio speaker, microphone, and one or more biological sensors, which may be biomedical or biometric sensors.

In certain embodiments, the biological sensors may include electrodes and associated amplifiers for measuring electrical signals of the body, including without limitation EEG signals from the brain and EKG/ECG signals from the heart. For example, EEG signals can be used to determine sleep or waking state. EKG/ECG signals can be used to determine heart rate, heart rate variability, identify heart rhythm characteristics, abnormalities, or other information. Temperature transducers may be provided for measuring temperature of the body. Other sensors include moisture sensors, which may be used to monitor sweating by the user. Optical sensors are also contemplated. Exemplary optical sensors may be used for sensing heart rate and blood oxygenation and other biomedical information. It will be recognized that the biological signals may be used for medical monitoring of the user as well as for biometric identification and authentication of the user.

The custom fit nature of the ear-fitting units 604, 606 serves as a first level discriminator for preventing an enemy or other unauthorized user from using the ear pieces in accordance with this disclosure because it is custom fit and, therefore, unlikely to fit into another user's ear. However, in preferred embodiments, biometric data sensed by the earpieces is used to identify the user and provide an inherency based authentication factor. In a preferred embodiment, biometric data related to the user's unique brain wave signals can be used to identify and authenticate the user.

The speaker, microphone, and one or more sensors are electrically coupled to a control module 608, which houses signal processing circuitry for receiving signals from the microphone and biological sensors and outputting an audio signal to the speaker. The speaker and microphone can be used for audio communication purpose. In certain embodiments, the speaker and microphone can also be used for biometric identification and authentication. For example, the speaker and microphone can be used to detect the acoustic properties or acoustic signature of the user's ear canal, which are unique to each individual.

In certain embodiments, the signal processing circuitry includes analog-to-digital and digital-to-analog conversion circuitry, which may be dedicated hardware ADCs and DACs, or, may be implemented in software or firmware in a microprocessor or microcontroller. The control module 608 also includes an RF (e.g., Bluetooth) transceiver for two-way wireless communication with an associated device or network. In certain embodiments, the RF transceiver is a Bluetooth receiver configured for communications with the Bluetooth transceiver 222 of the remote power supply 136 and/or the Bluetooth transceiver 253 of the firearm grip 236. The control module 608 also includes a battery compartment for receiving a battery power supply for powering operation of the wireless transceiver units and the signal processing circuitry.

The audio speaker component of the earpieces 600 can be used for audio communication purposes, hands free telephone usage, listening to audio, and so forth. The earpieces 600 may also employ a noise cancellation function to reduce background noise. In certain embodiments, the audio speaker component is used in conjunction with an external microphone to convert external sounds to an audio signal to the audio speakers of the earpieces 600. In certain embodiments, the external microphone is wireless microphone for transmitting audio information to the earpieces via the Bluetooth receiver in the control unit 608. In certain embodiments, the external microphone a directional microphone or microphone array for recording both sound and directional information of the sound. In certain embodiments, the processing electronics are configured to process the audio signal along with the directional information using a three-dimensional, binaural, or head-related transfer function (HRTF) algorithm sound processing algorithm which allows the user to interpret the sounds output by the audio speaker as coming from specific directions or points in space.

In certain embodiments, the sound processing electronics is configured to identify potentially threatening sounds and warn the user audibly and/or visually. An example of an audible warning might be a synthesized or prerecorded voice saying "enemy intruder approaching at 4 o'clock." Alternatively or additionally, if the user is employing the eyewear 412*a* (see FIG. 35) or 412 (see, e.g., FIG. 22), a visual warning may appear in the display screen 403. If the user is not using the eyewear 412 or 412*a*, a visual warning may be output to another display associated with the weapon system, such as the display 176. In certain embodiments, the earpieces 600 can be used for transmitting weapon settings and emergency settings via the Bluetooth interface in the control module 608.

Referring now to FIG. 35, there appears eyewear 412*a*, which include the ear pieces 600 as detailed above, configured to be worn when the user is wearing the glasses 412*a*, and which may be otherwise similar to the eyewear 412 discussed above by way of reference to FIGS. 21-25. The aforementioned control circuitry, transceiver, and power supply are housed in the housing 608*a* located on the temple piece.

Referring now to FIG. 36, there appears a piece of headwear 620 such as a military bump helmet, ballistic helmet, or the like. The headwear 620 includes earpieces 600 configured to be worn by the user when the helmet is worn. The aforementioned control circuitry, transceiver, and power supply are housed in the housing 608*b* located on the helmet. For example, the housing 608*b* may be attached to a rear connector on the helmet, or, incorporated into or attached to a shroud located on the front of the helmet 620. It will be recognized that other methods for attaching a power supply and electronics to a helmet are also contemplated.

Referring now to FIG. 37, there appears a standalone communications headset 630 comprising the earpieces 600 as detailed above and having a band, strap, or cable which extends over or behind the user's head. In the illustrated embodiment, the control circuitry and transceiver are housed within a control module housing 608*c* and the battery is housed within a battery housing 608*d*.

In certain embodiments, the earpieces 600 provide a brain computer interface for controlling operation of the associated weapon system. The brain wave signals from the electrodes in the earpiece 604 are sent to the signal processing electronics in the control module 608 and analyzed for a desired physiological movement or function. In this manner, the user can consciously manipulate his or her own brain activity, which is reflected in the brain wave signal transmitted to the processing electronics 608. The brain wave signal is monitored by the processing electronics until a signal or pattern representative of an operation or function to be performed on or by the weapon system disclosed is identified. If a brain wave signal or pattern that is representative of an operation or function to be performed on or by the weapon system, the processor in the processing electronics 608 generates an appropriate control signal which is transferred via the RF transmitter within the control unit 608 to a receiver such as transceiver 222 or 253. The control signal is then transferred via the bus 126 to a device coupled to the data bus 126.

For example, the operator can control the weapon system by consciously thinking of taking a certain action, e.g., turning on the flashlight 188 at 25% intensity. In certain embodiments, the use of brain wave signals to control the present weapon system may be provided in addition to dedicated buttons, switches, keypads, and for forth provided on the weapon system that can be manipulated manually to control operation of the weapon system herein. In other embodiments, however, it is contemplated that the number of dedicated keypads, buttons, switches, etc. can be reduced or eliminated in favor of the brain-computer interface provided by the earpieces 604. In certain embodiments, the weapon system herein is configured to restrict use to a particular individual or individuals.

As another example, it has been found that humans, such as a well-trained soldier, are capable of visually estimating a distance to a target with a reasonable degree of accuracy (e.g., +/−25 meters). Such estimates are suitable for a number of targeting applications. In this manner, the user can consciously manipulate his or her brain activity based on an estimated distance, which is reflected in the brain wave signal monitored by the processing electronics 608. A brain wave signal representative of estimated distance to a target is converted by the processing electronics 608 into an appropriate control signal which is transferred via the RF transmitter within the control unit 608 to a receiver such as transceiver 222 or 253. The control signal is then transferred via the bus 126 to a device coupled to the data bus 126. For example, the operator may automatically adjust the trajectory system of the reflex sight 160 by consciously estimating the target distance. As another example, a brain wave signal of approximate distance may be used to adjust a variable power scope to the proper power to engage an enemy. In certain embodiments, the use of brain wave signals for range estimation may be a functionality provided in addition to a dedicated range finder such as an optical range finder. In other embodiments, however, it is contemplated a range finding function implemented via the brain-computer interface function of the earpieces 600 would eliminate the need to have a rangefinder on the weapon.

The invention has been described with reference to the preferred embodiments. Obviously, modifications and alterations will occur to others upon reading and understanding the preceding detailed description. It is intended that the invention be construed as including all such modifications and alterations, insofar as they come within the scope of the appended claims or the equivalents thereof

What is claimed is:

1. A weapon system for controlling operation of a firearm comprising:
   a processor, the processor having an associated memory, the processor configured to receive sensor data from one or more sensors, the sensor data selected from the group consisting of:
      temperature data representative of a temperature of a barrel of the firearm;
      round count data representative of a number of rounds of ammunition fired by the firearm;
      barrel life expectancy data representative of wear accumulated by the barrel of the firearm;
      rate of fire data representative of a number of rounds of ammunition fired by the firearm per unit time;
      projectile velocity data representative of a velocity of the rounds of ammunition fired by the firearm;
      ammunition type data representative of a type of ammunition fired by the firearm;
      barrel whip data received from one or more strain gauges, the barrel whip data representative of one or more harmonic characteristics of the barrel of the firearm; and
      any combination of the foregoing;
   an optical reader, the optical reader configured to receive operator-identification information and transmit the operator-identification information to the processor; and
   a sighting system operably coupled to the processor, the sighting system including one or more aiming lasers, wherein the processor is configured to perform ballistics calculations and automatically adjust an angle of the one or more aiming lasers to improve accuracy of the sighting system based on said sensor data.

2. The weapon system of claim 1, wherein the optical reader is a camera configured to generate image signals.

3. The weapon system of claim 2, wherein the optical reader is configured to detect optically readable indicia.

4. The weapon system of claim 3, wherein the optically readable indicia is a bar code.

5. The weapon system of claim 2, wherein the camera comprises a facial-recognition system responsive to the image signals generated by the camera.

6. The weapon system of claim 5, wherein the facial recognition system is controllably coupled to the weapon system.

7. The weapon system of claim 2, wherein the operator-identification information is selected from the group consisting of facial feature data, iris recognition data, eye vein verification data, ocular feature data, machine-readable indicia.

8. The weapon system of claim 1, further comprising an accessory eyewear device.

9. The weapon system of claim 8, wherein the accessory eyewear device comprises a machine-readable indicia.

10. The weapon system of claim 8, wherein the accessory eyewear device comprises a near-eye display screen.

11. The weapon system of claim 10, wherein the near-eye display screen is configured to display one or more of the following: a system menu, sighting system menu options, sighting system statistical information, battery power level, user confirmation status, and user biometric data.

12. The weapon system of claim 8, wherein the machine-readable indicia is selected from the group consisting of: one dimensional bar code, two-dimensional bar code, and Quick Response (QR) code.

13. The weapon system of claim 9, wherein the camera is capable of reading the machine-readable indicia.

14. The weapon system of claim 2, wherein the camera is capable of tracking one or both of eye movement of a user and positioning of at least one eye of the user in relation to the weapon.

15. The weapon system of claim 8, the accessory eyewear device further comprising an in-ear communication system, the in-ear communication system comprising an electrical connector and an ear-fitting unit removably attachable to the electrical connector.

16. The weapon system of claim 15, wherein the electrical connector and the ear-fitting unit are removably attachable by a magnetic force.

17. The weapon system of claim 15, further comprising a control unit, the control unit in operable communication with the electrical connector.

18. The weapon system of claim 15, wherein the ear-fitting unit comprises an internal power supply.

19. The weapon system of claim 15, the ear-fitting unit comprising an external power supply.

20. The weapon system of claim 17, the ear-fitting unit comprising an exterior enclosure custom-fitted to a user's ear shape.

21. The weapon system of claim 20, the ear-fitting unit further comprising one or more biological sensors for generating signals representative of biometric information.

22. The weapon system of claim 21, wherein the biological sensors comprise a means for measuring electrical signals of a user's body.

23. The weapon system of claim 20, wherein the control unit comprises signal processing circuitry and an audio speaker, wherein the signal processing circuity is configured to receive the information representative of biometric information and generate an audible notification signal to the audio speaker.

24. The weapon system of claim 21, wherein the one or more biological sensors are selected from the group consisting of electrodes, temperature transducers, moisture sensors, optical sensors, heart rate sensor, and oxygen saturation sensor.

25. The weapon system of claim 20, the ear-fitting unit further comprising a microphone.

26. The weapon system of claim 25, wherein the microphone is configured to detect acoustic information representative of a user's acoustic signature.

27. The weapon system of claim 23, wherein the signal processing circuity comprises analog-to-digital and digital-to analog conversion circuitry.

28. The weapon system of claim 17, wherein the control unit further comprises a radio frequency (RF) transceiver.

29. The weapon system of claim 17, wherein the control unit further comprises a battery power supply.

30. The weapon system of claim 17, wherein the ear-fitting unit are configured to reduce background noise.

31. The weapon system of claim 24, further comprising an external microphone.

32. The weapon system of claim 31, wherein the signal processing circuitry is configured to generate an audio signal.

33. The weapon system of claim 32, wherein the audio signal is representative of directional information.

34. The weapon system of claim 33, wherein the directional information is processed by the signal processing circuity using sound processing algorithm selected from the group consisting of three-dimensional sound processing algorithm, binaural sound processing algorithm, and head-related transfer function sound processing algorithm.

35. The weapon system of claim 34, wherein the signal processing circuitry is configured to identify potentially threatening sounds and generate a warning signal.

36. The weapon system of claim 15, further comprising an eyewear in operable communication with the ear-fitting unit.

37. The weapon system of claim 36, wherein the electrical connector is attached to the eyewear.

38. The weapon system of claim 28, further comprise a brain computer interface for controlling operation of the weapon system.

39. The weapon system of claim 38, further comprising at least one electrode configured to generate brain wave signals, wherein the brain computer interface is configured to monitor and evaluate the brain wave signals.

40. The weapon system of claim 39, wherein the signal processing circuitry is configured to receive the generated brain wave signals and control operation of the weapon system in response to the generated brain signals.

41. The weapon system of claim 40, wherein the signal processing circuitry is further configured to generate a weapon system control signal and the RF transceiver is configured to receive the weapon system control signal.

42. The weapon system of claim 38, wherein the generated brain wave signals are representative of target distance information.

43. The weapon system of claim 6, further comprising a pistol grip, the pistol grip housing a safety mechanism in operable communication with the facial recognition system.

44. The weapon system of claim 1, further comprising:
a powered accessory rail interface having an upper accessory rail and a lower accessory rail;
a first accessory device removably attachable to the upper accessory rail, the first accessory device configured to receive electrical power and data signals over the powered accessory rail interface; and
a power supply electrically coupled to the powered accessory rail interface.

45. The weapon system of claim 44, further comprising a second accessory device removably attachable to the lower accessory rail, the second accessory device configured to receive electrical power and data signals over the powered accessory rail interface.

46. The weapon system of claim 44, wherein the power supply is a battery box electrically coupled to the lower accessory rail.

47. The weapon system of claim 46, further comprising a battery level circuit for determining a charge level of one or more batteries located in the battery box.

48. The weapon system of claim 46, further comprising an RF transceiver.

49. The weapons system of claim 48, wherein the RF transceiver is a Bluetooth transceiver.

50. The weapon system of claim 46, further comprising a first RFID reader.

51. The weapon system of claim 50, wherein the first RFID reader is located in the battery box.

52. The weapon system of claim 51, further comprising one or more ammunition magazines, each of the one or more ammunition magazines having an RFID chip readable by the RFID reader, the RFID chip configured to transmit information representative of ammunition type to the first RFID reader.

53. The weapon system of claim 44, wherein the power supply is housed in a pistol grip of the firearm.

54. The weapon system of claim 53, further comprising a remote programming fob configured to transmit one or more user program settings to the weapon system via the RF transmitter.

55. The weapon system of claim 54, wherein the remote programming fob is programmable with one or more of a computer, laptop, and mobile computing device.

56. The weapon system of claim 48, wherein the weapon system is programmable via the RF transceiver with one or more of a computer, laptop, mobile computing device, and accessory eyewear device.

57. The weapon system of claim 53, further comprising a second RFID reader.

58. The weapon system of claim 57, further comprising a tactical glove with a RFID chip readable by the second RFID reader, the RFID chip configured to transmit operator-identification information to the second RFID reader.

59. The weapon system of claim 58, further comprising a safety mechanism housed within the pistol grip, the safety mechanism configured to prevent operation of the firearm when the tactical glove with RFID chip is not in proximity to the second RFID reader.

60. The weapon system of claim 59, wherein the safety mechanism comprises a plunger and a solenoid configured to selectively lock and unlock a trigger mechanism of the firearm.

61. The weapon system of claim 53, wherein the pistol grip further comprises a battery level circuit for determining a charge level of one or more batteries located within the pistol grip.

62. The weapon system of claim 53, wherein the pistol grip includes one or more user input devices for controlling operation of the weapon system, the one or more user input devices selected from the group consisting of one or more buttons, a keypad, a rotary encoder, or any combination thereof.

63. The weapon system of claim 44, further comprising one or more sensors on the barrel for sensing one or more of: barrel temperatures, barrel strain, a projectile being fired, and a velocity of the projectile.

\* \* \* \* \*